(12) United States Patent
Siejko et al.

(10) Patent No.: US 7,972,275 B2
(45) Date of Patent: Jul. 5, 2011

(54) METHOD AND APPARATUS FOR MONITORING OF DIASTOLIC HEMODYNAMICS

(75) Inventors: Krzysztof Z. Siejko, Maple Grove, MN (US); Qingsheng Zhu, Little Canada, MN (US); Gerrard M. Carlson, Champlin, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 1337 days.

(21) Appl. No.: 10/334,694

(22) Filed: Dec. 30, 2002

(65) Prior Publication Data

US 2004/0127792 A1    Jul. 1, 2004

(51) Int. Cl.
*A61B 5/02* (2006.01)

(52) U.S. Cl. .......................................... 600/528; 600/513
(58) Field of Classification Search .................. 600/513, 600/528

See application file for complete search history.

(56) References Cited

U.S. PATENT DOCUMENTS

| | | | |
|---|---|---|---|
| 3,773,033 A | 11/1973 | Rodbard et al. | |
| 3,965,339 A | 6/1976 | Mount et al. | |
| 4,094,308 A * | 6/1978 | Cormier | 600/528 |
| 4,220,160 A | 9/1980 | Kimball et al. | |
| 4,289,141 A | 9/1981 | Cormier | |
| 4,428,378 A | 1/1984 | Anderson et al. | |
| 4,428,380 A | 1/1984 | Wong et al. | 128/715 |
| 4,446,872 A | 5/1984 | Marsoner et al. | |
| 4,548,204 A | 10/1985 | Groch et al. | |
| 4,586,514 A * | 5/1986 | Schlager et al. | 600/586 |
| 4,628,939 A | 12/1986 | Little et al. | 128/696 |
| 4,649,930 A | 3/1987 | Groch et al. | |
| 4,674,518 A | 6/1987 | Salo | 128/695 |
| 4,686,987 A | 8/1987 | Salo et al. | 128/419 PG |
| 4,702,253 A | 10/1987 | Nappholz et al. | |
| 4,712,179 A | 12/1987 | Heimer | 364/417 |
| 4,763,646 A | 8/1988 | Lekholm | |
| 4,777,960 A | 10/1988 | Berger et al. | 600/519 |
| 4,796,639 A | 1/1989 | Snow et al. | |

(Continued)

FOREIGN PATENT DOCUMENTS

EP      0297675 A1    1/1989

(Continued)

OTHER PUBLICATIONS

Aaron, S. D., et al., "How accurate is spirometry at predicting restrictive pulmonary impairment?", *Chest*, 115(3), (Mar. 1999), 869-873.

(Continued)

*Primary Examiner* — Niketa I Patel
*Assistant Examiner* — Joseph Stoklosa
(74) *Attorney, Agent, or Firm* — Schwegman, Lundberg & Woessner, P.A.

(57) ABSTRACT

A cardiac rhythm management system provides for ambulatory monitoring of hemodynamic performance based on quantitative measurements of heart sound related parameters for diagnostic and therapeutic purposes. Monitoring of such heart sound related parameters allows the cardiac rhythm management system to determine a need for delivering a therapy and/or therapy parameter adjustments based on conditions of a heart. This monitoring also allows a physician to observe or assess the hemodynamic performance for diagnosing and making therapeutic decisions. Because the conditions of the heart may fluctuate and may deteriorate significantly between physician visits, the ambulatory monitoring, performed on a continuous or periodic basis, ensures a prompt response by the cardiac rhythm management system that may save a life, prevent hospitalization, or prevent further deterioration of the heart.

43 Claims, 7 Drawing Sheets

U.S. PATENT DOCUMENTS

| | | | |
|---|---|---|---|
| 4,809,697 A | 3/1989 | Causey, III et al. | 128/419 PT |
| 4,825,869 A | 5/1989 | Sasmor et al. | 128/419 PT |
| 4,899,751 A | 2/1990 | Cohen | |
| 4,905,706 A | 3/1990 | Duff et al. | 128/701 |
| 4,915,113 A | 4/1990 | Holman | |
| 4,928,688 A | 5/1990 | Mower | 128/419 PG |
| 4,945,909 A | 8/1990 | Fearnot et al. | 128/419 PG |
| 4,967,760 A * | 11/1990 | Bennett et al. | 600/528 |
| 4,981,139 A | 1/1991 | Pfohl | 128/671 |
| 4,989,611 A | 2/1991 | Zanetti et al. | |
| 5,010,889 A | 4/1991 | Bredesen et al. | |
| 5,012,815 A | 5/1991 | Bennett, Jr. et al. | |
| 5,025,809 A | 6/1991 | Johnson et al. | 128/715 |
| 5,097,831 A | 3/1992 | Lekholm | 128/419 D |
| 5,137,019 A | 8/1992 | Pederson et al. | 128/419 |
| 5,159,932 A | 11/1992 | Zanetti et al. | |
| 5,179,947 A | 1/1993 | Meyerson et al. | 128/419 PG |
| 5,190,035 A | 3/1993 | Salo et al. | 128/419 |
| 5,218,969 A | 6/1993 | Bredesen et al. | |
| 5,226,413 A | 7/1993 | Bennett et al. | 128/419 PG |
| 5,251,626 A | 10/1993 | Nickolls et al. | 607/14 |
| 5,282,838 A | 2/1994 | Hauser et al. | 607/9 |
| 5,284,136 A | 2/1994 | Hauck et al. | 607/24 |
| 5,292,341 A | 3/1994 | Snell | 607/30 |
| 5,301,679 A | 4/1994 | Taylor | 128/773 |
| 5,321,618 A | 6/1994 | Gessman | 364/413.06 |
| 5,334,222 A | 8/1994 | Salo et al. | 607/17 |
| 5,337,752 A | 8/1994 | Reeves | 128/700 |
| 5,365,932 A | 11/1994 | Greenhut | |
| 5,372,607 A | 12/1994 | Stone et al. | 607/30 |
| 5,391,190 A | 2/1995 | Pederson et al. | 607/23 |
| 5,417,717 A | 5/1995 | Salo et al. | 607/18 |
| 5,421,830 A | 6/1995 | Epstein et al. | 607/30 |
| 5,472,453 A | 12/1995 | Alt | |
| 5,487,752 A | 1/1996 | Salo et al. | 607/17 |
| 5,496,361 A | 3/1996 | Moberg et al. | |
| 5,540,727 A | 7/1996 | Tockman et al. | 607/18 |
| 5,544,661 A * | 8/1996 | Davis et al. | 600/513 |
| 5,549,654 A | 8/1996 | Powell | 607/32 |
| 5,554,177 A | 9/1996 | Kieval et al. | 607/17 |
| 5,584,868 A | 12/1996 | Salo et al. | 607/17 |
| 5,593,431 A | 1/1997 | Sheldon | |
| 5,594,638 A | 1/1997 | Iliff | 395/203 |
| 5,607,460 A | 3/1997 | Kroll et al. | 607/30 |
| 5,630,835 A | 5/1997 | Brownlee | 607/60 |
| 5,674,256 A | 10/1997 | Carlson | 607/17 |
| 5,685,317 A | 11/1997 | Sjostrom | |
| 5,687,738 A | 11/1997 | Shapiro et al. | 128/715 |
| 5,690,690 A | 11/1997 | Nappholz et al. | 607/30 |
| 5,697,375 A | 12/1997 | Hickey | |
| 5,697,959 A | 12/1997 | Poore | |
| 5,700,283 A | 12/1997 | Salo | 607/17 |
| 5,725,562 A | 3/1998 | Sheldon | |
| 5,792,195 A | 8/1998 | Carlson et al. | 607/17 |
| 5,800,473 A | 9/1998 | Faisandier | 607/59 |
| 5,833,623 A | 11/1998 | Mann et al. | 600/523 |
| 5,836,987 A | 11/1998 | Baumann et al. | 607/17 |
| 5,860,918 A | 1/1999 | Schradi et al. | 600/300 |
| 5,860,933 A | 1/1999 | Don Michael | 600/528 |
| 5,891,178 A | 4/1999 | Mann et al. | 607/27 |
| 5,935,081 A | 8/1999 | Kadhiresan | 600/513 |
| 5,991,657 A | 11/1999 | Kim | |
| 5,991,661 A | 11/1999 | Park et al. | |
| 6,002,777 A * | 12/1999 | Grasfield et al. | 381/67 |
| 6,015,388 A | 1/2000 | Sackner et al. | 600/529 |
| 6,016,442 A | 1/2000 | Hsu et al. | 600/518 |
| 6,022,322 A | 2/2000 | Prutchi | 600/506 |
| 6,026,324 A | 2/2000 | Carlson | |
| 6,044,297 A | 3/2000 | Sheldon et al. | |
| 6,044,298 A | 3/2000 | Salo et al. | 607/17 |
| 6,044,299 A | 3/2000 | Nilsson | 607/19 |
| 6,045,513 A | 4/2000 | Stone et al. | |
| 6,053,872 A | 4/2000 | Mohler | |
| 6,058,329 A | 5/2000 | Salo et al. | 607/17 |
| 6,064,910 A | 5/2000 | Andersson et al. | |
| 6,077,227 A | 6/2000 | Miesel | |
| 6,091,990 A | 7/2000 | Hsu et al. | 607/5 |
| 6,104,949 A | 8/2000 | Pitts Crick et al. | |
| 6,144,880 A | 11/2000 | Ding et al. | 607/23 |
| 6,152,884 A | 11/2000 | Bjorgaas | |
| 6,161,042 A | 12/2000 | Hartley et al. | 607/20 |
| 6,168,563 B1 | 1/2001 | Brown | 600/301 |
| 6,190,324 B1 | 2/2001 | Kieval et al. | 600/483 |
| 6,193,668 B1 | 2/2001 | Chassaing et al. | 600/481 |
| 6,251,126 B1 | 6/2001 | Ottenhoff et al. | |
| 6,264,611 B1 | 7/2001 | Ishikawa et al. | |
| 6,269,269 B1 | 7/2001 | Ottenhoff et al. | |
| 6,273,856 B1 | 8/2001 | Sun et al. | 600/300 |
| 6,275,727 B1 | 8/2001 | Hopper et al. | 600/513 |
| 6,278,894 B1 | 8/2001 | Salo et al. | 600/547 |
| 6,280,409 B1 | 8/2001 | Stone et al. | 604/67 |
| 6,298,269 B1 | 10/2001 | Sweeney | |
| 6,312,378 B1 | 11/2001 | Bardy | |
| 6,351,672 B1 | 2/2002 | Park et al. | |
| 6,351,673 B1 | 2/2002 | Ding et al. | 607/24 |
| 6,360,127 B1 | 3/2002 | Ding et al. | 607/23 |
| 6,361,522 B1 | 3/2002 | Scheiner et al. | 604/67 |
| 6,366,811 B1 | 4/2002 | Carlson | |
| 6,368,283 B1 | 4/2002 | Xu et al. | |
| 6,370,424 B1 | 4/2002 | Prutchi | 600/547 |
| 6,383,136 B1 | 5/2002 | Jordan | 600/300 |
| 6,409,675 B1 | 6/2002 | Turcott | 600/508 |
| 6,411,840 B1 | 6/2002 | Bardy | |
| 6,415,033 B1 | 7/2002 | Halleck et al. | |
| 6,438,407 B1 | 8/2002 | Ousdigian et al. | 600/510 |
| 6,440,082 B1 | 8/2002 | Joo et al. | |
| 6,459,929 B1 | 10/2002 | Hopper et al. | |
| 6,466,821 B1 | 10/2002 | Pianca et al. | |
| 6,477,406 B1 | 11/2002 | Turcott | 600/518 |
| 6,478,746 B2 | 11/2002 | Chassaing et al. | 600/504 |
| 6,480,733 B1 * | 11/2002 | Turcott | 600/516 |
| 6,491,639 B1 | 12/2002 | Turcott | 600/508 |
| 6,520,924 B2 | 2/2003 | Lee | 600/586 |
| 6,527,729 B1 | 3/2003 | Turcott | 600/528 |
| 6,542,775 B2 | 4/2003 | Ding et al. | 607/24 |
| 6,575,916 B2 | 6/2003 | Halleck et al. | 600/528 |
| 6,625,493 B2 | 9/2003 | Kroll et al. | |
| 6,626,842 B2 | 9/2003 | Oka | 600/528 |
| 6,643,548 B1 * | 11/2003 | Mai et al. | 607/17 |
| 6,650,940 B1 | 11/2003 | Zhu et al. | |
| 6,658,292 B2 | 12/2003 | Kroll et al. | |
| 6,665,564 B2 | 12/2003 | Lincoln et al. | |
| 6,666,826 B2 | 12/2003 | Salo et al. | |
| 6,684,103 B2 | 1/2004 | Ding et al. | 607/23 |
| 6,719,701 B2 | 4/2004 | Lade | |
| 6,733,464 B2 | 5/2004 | Olbrich et al. | |
| 6,752,765 B1 | 6/2004 | Jensen et al. | |
| 6,792,308 B2 | 9/2004 | Corbucci | |
| 6,795,732 B2 | 9/2004 | Stadler et al. | |
| 6,810,284 B1 | 10/2004 | Bradley | |
| 6,810,287 B2 | 10/2004 | Zhu et al. | |
| 6,824,519 B2 | 11/2004 | Narimatsu et al. | |
| 6,827,690 B2 | 12/2004 | Bardy | |
| 6,830,548 B2 | 12/2004 | Bonnet et al. | |
| 6,845,263 B2 | 1/2005 | Kawaguchi | |
| 6,885,889 B2 | 4/2005 | Chinchoy | |
| 6,913,577 B2 | 7/2005 | Bardy | |
| 6,942,622 B1 | 9/2005 | Turcott | |
| 6,961,617 B1 | 11/2005 | Snell | |
| 6,963,777 B2 | 11/2005 | Lincoln et al. | |
| 7,010,342 B2 | 3/2006 | Galen et al. | |
| 7,043,305 B2 | 5/2006 | KenKnight et al. | |
| 7,065,397 B2 | 6/2006 | Galen et al. | |
| 7,072,708 B1 | 7/2006 | Andersen et al. | |
| 7,074,195 B2 | 7/2006 | Nelson et al. | |
| 7,079,895 B2 | 7/2006 | Verbeek et al. | |
| 7,079,896 B1 | 7/2006 | Park et al. | |
| 7,110,804 B2 | 9/2006 | Baumer et al. | |
| 7,113,825 B2 | 9/2006 | Pastore et al. | |
| 7,115,096 B2 | 10/2006 | Siejko et al. | |
| 7,123,962 B2 | 10/2006 | Siejko et al. | |
| 7,139,609 B1 | 11/2006 | Min et al. | |
| 7,177,685 B2 | 2/2007 | Lincoln et al. | |
| 7,206,636 B1 | 4/2007 | Turcott | |
| 7,366,568 B2 | 4/2008 | Pastore et al. | |
| 7,387,610 B2 | 6/2008 | Stahmann et al. | |
| 7,400,928 B2 | 7/2008 | Hatlestad | |

| | | |
|---|---|---|
| 7,404,802 B2 | 7/2008 | Siejko et al. |
| 7,493,162 B2 | 2/2009 | Girouard et al. |
| 7,582,061 B2 | 9/2009 | Li et al. |
| 7,585,279 B2 | 9/2009 | Carlson et al. |
| 7,662,101 B2 | 2/2010 | Lee et al. |
| 7,668,594 B2 | 2/2010 | Brockway et al. |
| 7,713,213 B2 | 5/2010 | Siejko et al. |
| 7,736,319 B2 | 6/2010 | Patangay et al. |
| 7,751,890 B2 | 7/2010 | McCabe et al. |
| 7,774,057 B2 | 8/2010 | Pastore et al. |
| 7,780,606 B2 | 8/2010 | Carlson et al. |
| 7,844,334 B2 | 11/2010 | Maile et al. |
| 2001/0007053 A1 | 7/2001 | Bardy ........................... 600/300 |
| 2002/0001390 A1 | 1/2002 | Kawaguchi |
| 2002/0019586 A1 | 2/2002 | Teller et al. .................. 600/300 |
| 2002/0026103 A1 | 2/2002 | Norris et al. ................. 600/300 |
| 2002/0026223 A1 | 2/2002 | Riff et al. ........................ 607/27 |
| 2002/0035337 A1 | 3/2002 | Oka |
| 2002/0072684 A1* | 6/2002 | Stearns ........................ 600/528 |
| 2002/0082645 A1 | 6/2002 | Sweeney |
| 2002/0107450 A1 | 8/2002 | Ogura |
| 2002/0120298 A1 | 8/2002 | Kramer et al. |
| 2002/0128563 A1 | 9/2002 | Carlson et al. |
| 2002/0147401 A1 | 10/2002 | Oka |
| 2002/0151812 A1 | 10/2002 | Scheiner et al. |
| 2002/0151938 A1 | 10/2002 | Corbucci ........................ 607/25 |
| 2003/0055352 A1 | 3/2003 | Hayek et al. |
| 2003/0055461 A1 | 3/2003 | Girouard et al. |
| 2003/0069608 A1 | 4/2003 | Sweeney |
| 2003/0072458 A1 | 4/2003 | Halleck et al. |
| 2003/0078624 A1 | 4/2003 | Carlson et al. |
| 2003/0093002 A1 | 5/2003 | Kuo |
| 2003/0093003 A1 | 5/2003 | Watrous et al. |
| 2003/0105496 A1 | 6/2003 | Yu et al. |
| 2003/0120159 A1 | 6/2003 | Mohler |
| 2003/0125774 A1 | 7/2003 | Salo ................................ 607/21 |
| 2003/0144702 A1 | 7/2003 | Yu et al. ......................... 607/17 |
| 2003/0144703 A1 | 7/2003 | Yu et al. ......................... 607/17 |
| 2003/0158492 A1 | 8/2003 | Sheldon et al. |
| 2003/0158584 A1 | 8/2003 | Cates et al. |
| 2003/0171791 A1 | 9/2003 | KenKnight et al. |
| 2003/0176896 A1 | 9/2003 | Lincoln et al. |
| 2003/0191503 A1 | 10/2003 | Zhu et al. |
| 2003/0208240 A1 | 11/2003 | Pastore et al. .................. 607/17 |
| 2003/0216620 A1 | 11/2003 | Jain et al. |
| 2003/0229289 A1 | 12/2003 | Mohler |
| 2004/0024423 A1 | 2/2004 | Lincoln et al. |
| 2004/0039295 A1 | 2/2004 | Olbrich et al. |
| 2004/0039419 A1 | 2/2004 | Stickney et al. |
| 2004/0039420 A1 | 2/2004 | Jayne et al. |
| 2004/0064056 A1 | 4/2004 | Ogura |
| 2004/0078059 A1 | 4/2004 | Ding et al. |
| 2004/0078060 A1 | 4/2004 | Ding et al. |
| 2004/0102712 A1 | 5/2004 | Belalcazar et al. |
| 2004/0106960 A1 | 6/2004 | Siejko et al. .................... 607/17 |
| 2004/0106961 A1 | 6/2004 | Siejko et al. .................... 607/17 |
| 2004/0106962 A1 | 6/2004 | Mai et al. |
| 2004/0111040 A1 | 6/2004 | Ni et al. |
| 2004/0122484 A1 | 6/2004 | Hatlestad et al. ............... 607/60 |
| 2004/0127792 A1 | 7/2004 | Siejko et al. |
| 2004/0138572 A1 | 7/2004 | Thiagarajan |
| 2004/0167417 A1 | 8/2004 | Schulhauser et al. |
| 2004/0215264 A1 | 10/2004 | van Bentem |
| 2004/0225332 A1 | 11/2004 | Gebhardt et al. |
| 2004/0236239 A1 | 11/2004 | Murray et al. |
| 2004/0243192 A1 | 12/2004 | Hepp et al. |
| 2004/0254481 A1 | 12/2004 | Brodnick |
| 2004/0267147 A1 | 12/2004 | Sullivan |
| 2004/0267148 A1 | 12/2004 | Arand et al. |
| 2005/0004485 A1 | 1/2005 | Crosby et al. |
| 2005/0027323 A1 | 2/2005 | Mulligan et al. |
| 2005/0033190 A1 | 2/2005 | Bauer |
| 2005/0060001 A1 | 3/2005 | Singhal et al. |
| 2005/0065448 A1 | 3/2005 | Stahmann et al. |
| 2005/0065556 A1 | 3/2005 | Reghabi et al. |
| 2005/0090870 A1 | 4/2005 | Hine et al. |
| 2005/0102001 A1 | 5/2005 | Maile et al. |
| 2005/0102002 A1 | 5/2005 | Salo et al. |
| 2005/0148896 A1 | 7/2005 | Siejko et al. |
| 2005/0148897 A1 | 7/2005 | Cho et al. |
| 2005/0149136 A1 | 7/2005 | Siejko et al. |
| 2005/0203579 A1 | 9/2005 | Sowelam et al. |
| 2005/0222515 A1 | 10/2005 | Polyshchuk et al. |
| 2005/0256542 A1 | 11/2005 | Pastore et al. |
| 2006/0020294 A1 | 1/2006 | Brockway et al. |
| 2006/0020295 A1 | 1/2006 | Brockway et al. |
| 2006/0025699 A1 | 2/2006 | Maile et al. |
| 2006/0030892 A1 | 2/2006 | Kadhiresan et al. |
| 2006/0161070 A1 | 7/2006 | Siejko et al. |
| 2006/0259087 A1 | 11/2006 | Baynham et al. |
| 2006/0259088 A1 | 11/2006 | Pastore et al. |
| 2006/0270939 A1 | 11/2006 | Wariar et al. |
| 2006/0282000 A1 | 12/2006 | Zhang et al. |
| 2007/0078491 A1 | 4/2007 | Siejko et al. |
| 2007/0150005 A1 | 6/2007 | Sih et al. |
| 2007/0239218 A1 | 10/2007 | Carlson et al. |
| 2008/0071315 A1 | 3/2008 | Baynham et al. |
| 2008/0103406 A1 | 5/2008 | Kameli |
| 2008/0119749 A1 | 5/2008 | Haro et al. |
| 2010/0099997 A1 | 4/2010 | Siejko et al. |
| 2010/0249863 A1 | 9/2010 | Carlson et al. |

FOREIGN PATENT DOCUMENTS

| | | |
|---|---|---|
| EP | 0709058 A1 | 1/1996 |
| EP | 1179317 A2 | 2/2002 |
| EP | 1247485 A1 | 10/2002 |
| JP | 61-202653 A | 9/1986 |
| JP | 63-109103 U | 7/1988 |
| JP | 63-290544 A | 11/1988 |
| JP | 03015441 | 1/1991 |
| JP | 06-277189 A | 10/1994 |
| JP | 2000-060846 A | 2/2000 |
| JP | 2000-316825 A | 11/2000 |
| JP | 2001145606 | 5/2001 |
| WO | WO-0041765 | 7/2000 |
| WO | WO-0041766 | 7/2000 |
| WO | WO-01/03575 | 1/2001 |
| WO | WO-01/24876 A1 | 4/2001 |
| WO | WO-0122885 A1 | 4/2001 |
| WO | WO-0124876 A1 | 4/2001 |
| WO | WO-0156651 A1 | 8/2001 |
| WO | WO-01/67948 A2 | 9/2001 |
| WO | WO-0167948 A2 | 9/2001 |
| WO | WO-2004/012815 A1 | 2/2004 |
| WO | WO-2004050178 A1 | 6/2004 |
| WO | WO-2004/060483 A1 | 7/2004 |
| WO | WO-2005/122902 A1 | 12/2005 |
| WO | WO-2006/028575 A2 | 3/2006 |
| WO | WO-2006078757 A1 | 7/2006 |
| WO | WO-2006127594 A2 | 11/2006 |

OTHER PUBLICATIONS

Bulgrin, J. R., et al., "Comparison of Short-Time Fourier, Wavelet and Time-Domain Analyses of Intracardiac Sounds", *Biomedical Sciences Instrumentation*, 29, (1993), 465-472.

Leatham, A , "Splitting of the First and Second Heart Sounds", *Lancet*, 267 (6839), (Sep. 25, 1954), 607-614.

Obaidat, M. S., et al., "Performance of the Short-Time Fourier Transform and Wavelet Transform to Phonocardiogram Signal Analysis", *Proceedings of the 1992 ACM/SIGAPP Symposium on Applied Computing ACM*, Applied Computing: Technological Challenges of the 1990s, (1992), 856-862.

Wood, J. C. et al., "Time-Frequency Transforms: A New Approach to First Heart Sound Frequency Dynamics", *IEEE Transactions on Biomedical Engineering*, 39 (7), IEEE Service Center, US, (Jul. 1, 1992), 730-740.

Ding, Jiang , et al., "Cardiac Pacing Using Adjustable Atrio-Ventricular Delays", U.S. Appl. No. 10/008,830, (Dec. 7, 2001), 1-42.

Ding, Jiang , et al., "Cardiac Pacing Using Adjustable Atrio-Ventricular Delays", U.S. Appl. No. 10/243,811, (Sep. 13, 2002), 1-39.

Yu, Yinghong , et al., "Method and Apparatus for Optimizing Stroke Volume During DDD Resynchronization Therapy Using Adjustable Atrio-Ventricular Delays", U.S. Appl. No. 10/314,899, (Dec. 9, 2002), 1-50.

Yu, Yinghong, et al., "Method and Apparatus for Optimizing Ventricular Synchrony During DDD Resynchronization Therapy Using Adjustable Atrio-Ventricular Delays", U.S. Appl. No. 10/314,910,(Dec. 9, 2002), 1-50.

Barbaro, V., et al., "A portable unit for remote monitoring of pacemaker patients", *Journal of Telemedicine and Telecare*, 3(2), (1997),96-102.

Brockway, M. et al., "Method and Apparatus for Monitoring Heart Failure Patients With Cardiopulmonary Comorbidities", U.S. Appl. No. 10/897,856, filed Jul. 23, 2004, 54 pgs.

Brockway, Marina, et al., "Method and Apparatus for Optimization of Cardiac Resynchronization Therapy Using Heart Sounds", U.S. Appl. No. 10/865,498, filed Jun. 10, 2004, 45 pgs.

Girouard, Steven D., et al., "Cardiac Rhythm Management Systems and Methods Predicting Congestive Heart Failure Status", filed: Aug. 6, 2002 U.S. Appl. No. 10/213,268, 33 pgs.

Hatlestad, John, "Methods and Devices for Detection of Context When Addressing a Medical Condition of a Patient", filed: Oct. 11, 2002 U.S. Appl. No. 10/269,611,29 pages.

Hutten, H., et al., "Cardiac Telemonitoring through the Linkage of Close-up Telemetry and Internet Transmission", *Institute for Electro- and Biomedical Technology, Technical University of Graz Inffeldgasse, 42 English Abstract*, (1997), 67-69.

KenKnight, Bruce H., et al., "Method and Apparatus for Establishing Context Among Events and Optimizing Implanted Medical Device Performance", filed Mar. 6, 2002 U.S. Appl. No. 10/093,353, 43 pgs.

Maile, Keith R., et al., "A Dual-Use Sensor for Rate Responsive Pacing and Heart Sound Monitoring", U.S. Appl. No. 10/703,175, filed Nov. 6, 2003, 41 pgs.

Maile, Keith R., et al., "Determining a Patient's Posture From Mechanical Vibrations of the Heart", U.S. Appl. No. 10/900,570, filed Jul. 28, 2004, 24 pgs.

Siejko, Krzysztof Z., et al., "A Third Heart Sound Activity Index for Heart Failure Monitoring", U.S. Appl. No. 10/746,874, filed Dec. 24, 2003, 41 pgs.

Siejko, Krzysztof Z., et al., "Method and Apparatus for Third Heart Sound Detection", U.S. Appl. No. 10/746,853, filed Dec. 24, 2003 40 pgs.

Smith, Damon, et al., "Influence of the Aortic Component of the Second Heart Sound on Left Ventricular Maximal Negative dP/dt in the Dog", *Am. J. Cardiol.*, 55: 205, (1985),205-209.

Zhu, Qingsheng, et al., "Method and Apparatus for Determining Changes in Heart Failure Status", filed Nov. 15, 2001 U.S. Appl. No. 10/001,223, 22 pgs.

Siejko, K. Z., et al., "Method for Correction of Posture Dependence on Heart Sounds", U.S. Appl. No. 11/037,275, filed Jan. 18, 2005, 26 pgs.

Wariar, R., et al., "Systems and Methods for Multi-Axis Cardiac Vibration Measurements", U.S. Appl. No. 11/135,985, filed May 24, 2004.

Zhang, Y., et al., "Ischemia Detection Using a Heart Sound Sensor", U.S. Appl. No. 11/148,107, filed Jun. 8, 2005, 41 pgs.

Amende, I., "Hemodynamics in ischemia: diastolic phase", *Z. Kardiol.*, 73 Suppl 2, [Article in German],(1984),127-33.

Collins, Sean, "Diagnostic Utility of an S3 in Dyspneic ED Patients", *Inovise Medical Inc, University of Cincinnati Medical Center*, (2005),6 Pages.

Marcus, G. M., et al., "Association Between Phonocardiographic Third and Fourth Heart Sounds and Objective Measures of Left Ventricular Function", *JAMA*, 293(18), (May 11, 2005),2238-44.

"U.S. Appl. No. 10/746,874 Notice of Allowance mailed May 19, 2006", 13 pgs.

"U.S. Appl. No. 10/865,498 Non-Final Office Action mailed Sep. 11, 2006", 11 pgs.

"U.S. Appl. No. 10/865,498 Notice of Allowance mailed Dec. 6, 2006", 12 pgs.

"U.S. Appl. No. 10/865,498 Response to Non-Final Office Action filed Oct. 24, 2006", 23 pgs.

"Japanese application Serial No. 2004-565783 Office Action Mailed Nov. 11, 2009", 2 pgs.

"European Application Serial No. 03800278.8, Communication dated Oct. 17, 2007", 4 pgs.

"European Application Serial No. 03800278.8, Response filed Feb. 18, 2008 to Communication dated Oct. 17, 2007", 14 pgs.

"International Application Serial No. PCT/US03/41481, International Search Report mailed Jun. 4, 2004", 7 pgs.

"Japanese Application No. 2004-565783, Office Action mailed Mar. 11, 2010", 2 pgs.

"Japanese Application Serial No. 2004-565783, Amendment and Argument filed Feb. 5, 2010 to Office Action Mailed Nov. 11, 2009", (w/ English Translation of Amended Claims), 14 pgs.

"Eureopean Serial Application No. 10158651.9, Search Report mailed on Jul. 29, 2010", 6 pgs.

"Japanese Application Serial No. 2004-565783, Notice of Allowance mailed Aug. 9, 2010", 2 pgs.

* cited by examiner

METHOD AND APPARATUS FOR MONITORING OF DIASTOLIC HEMODYNAMICS

CROSS-REFERENCE TO RELATED APPLICATIONS

This application is related to co-pending, commonly assigned Siejko et al. U.S. patent application Ser. No. 10/307,896, entitled "PHONOCARDIOGRAPHIC IMAGE-BASED ATRIOVENTRICULAR DELAY OPTIMIZATION," filed Dec. 2, 2002, now issued as U.S. Pat. No. 7,123,962, which is hereby incorporated by reference.

TECHNICAL FIELD

This document relates generally to cardiac rhythm management systems and particularly, but not by way of limitation, to such a system sensing heart sounds for monitoring, diagnosis, and therapy control.

BACKGROUND

A heart is the center of a person's circulatory system. It includes a complex electro-mechanical system performing two major pumping functions. The left portions of the heart, including the left atrium and the left ventricle, draw oxygenated blood from the lungs and pump it to the organs of the body to provide the organs with their metabolic needs for oxygen. The right portions of the heart, including the right atrium and the right ventricle, draw deoxygenated blood from the organs and pump it into the lungs where the blood gets oxygenated. These mechanical pumping functions are accomplished by contractions of the myocardium (heart muscles). In a normal heart, the sinus node, the heart's natural pacemaker, generates electrical signals, called action potentials, that propagate through an electrical conduction system to various regions of the heart to excite myocardial tissues in these regions. Coordinated delays in the propagations of the action potentials in a normal electrical conduction system cause the various regions of the heart to contract in synchrony such that the pumping functions are performed efficiently. Thus, the normal pumping functions of the heart, indicated by hemodynamic performance, require a normal electrical system to generate the action potentials and deliver them to designated portions of the myocardium with proper timing, a normal myocardium capable of contracting with sufficient strength, and a normal electro-mechanical association such that all regions of the heart are excitable by the action potentials.

The function of the electrical system is indicated by electrocardiography (ECG) with at least two electrodes placed in or about the heart to sense the action potentials. When the heart beats irregularly or otherwise abnormally, one or more ECG signals indicate that contractions at various cardiac regions are chaotic and unsynchronized. Such conditions are known as cardiac arrhythmias. Cardiac arrhythmias result in a reduced pumping efficiency of the heart, and hence, diminished blood circulation. Examples of such arrhythmias include bradyarrhythmias, that is, hearts that beat too slowly or irregularly, and tachyarrhythmias, that is, hearts that beat too quickly. A patient may also suffer from weakened contraction strength related to deterioration of the myocardium. This further reduces the pumping efficiency. For example, a heart failure patient suffers from an abnormal electrical conduction system with excessive conduction delays and deteriorated heart muscles that result in asynchronous and weak heart contractions, and hence, reduced pumping efficiency, or poor hemodynamic performance. Thus, in addition to ECG, the function of the mechanical system and the electro-mechanical association need to be measured to assess the overall pumping performance of the heart.

Characteristics of heart sounds are known to be indicative of various mechanical properties and activities of the heart. Measurements performed with synchronously recorded ECG and heart sounds provide for quantitative indications of the electro-mechanical association. For example, amplitudes of the third heart sound (S3) and fourth heart sound (S4) are related to filling pressures of the left ventricle during diastole. Fundamental frequencies of S3 and S4 are related to ventricular stiffness and dimension. Chronic changes in S3 amplitude is correlated to left ventricular chamber stiffness and degree of restrictive filling. Change in the interval between atrial contraction and S4 is correlated to the changes in left ventricular end of diastolic pressure. Such parameters, being correlated to the heart's mechanical properties and electro-mechanical association, quantitatively indicate abnormal cardiac conditions, including degrees of severity, and need of appropriate therapies.

For these and other reasons, there is a need for a system providing for cardiac therapy based on parameters related to heart sounds.

SUMMARY

A cardiac rhythm management system provides for ambulatory monitoring of hemodynamic performance based on quantitative measurements of heart sound related parameters for diagnostic and therapeutic purposes. Monitoring of such heart sound related parameters allows the cardiac rhythm management system to determine a need for delivering a therapy and/or therapy parameter adjustments based on conditions of a heart. This monitoring also allows a physician to observe or assess the hemodynamic performance for diagnosing and making therapeutic decisions. Because the conditions of the heart may fluctuate and may deteriorate significantly between physician visits, the ambulatory monitoring, performed on a continuous or periodic basis, ensures a prompt response by the cardiac rhythm management system that may save a life, prevent hospitalization, or prevent further deterioration of the heart.

In one embodiment, a system includes an acoustic sensor, a cardiac sensing circuit, a heart sound detector, a parameter generator, a processor, and a therapy circuit. The acoustic sensor senses an acoustic energy and produces an acoustic sensor signal indicative heart sounds. The cardiac sensing circuit senses a cardiac signal indicative of cardiac electrical events. The heart sound detector detects selected heart sounds based on the acoustic sensor signal and the cardiac signal. The parameter generator generates values of at least one predetermined parameter related to the selected heart sounds. The processor includes a trending analyzer that produces and analyzes at least one trend related to the selected heart sounds based on the values of the predetermined parameter. The therapy circuit delivers cardiac therapy with at least one therapy parameter determined based on the trend.

In another embodiment, an acoustic energy is sensed to produce an acoustic sensor signal indicative heart sounds. One or more cardiac signals indicative of cardiac electrical events are also sensed. Selected heart sounds are detected. Parameter values related to the selected heart sounds and selected cardiac electrical events are generated. Selected parameter values, which are associated with one or more types of the selected heart sounds, are analyzed to produce at least one trend. A therapy, with at least one parameter determined based on the trend, is delivered.

In yet another embodiment, a cardiac rhythm management system includes an implantable device. The implantable device includes an acoustic sensor, a cardiac sensing circuit, a gating module, a heart sound detector, a measurement module, and a therapy circuit. The acoustic sensor senses an acoustic energy to produce an acoustic sensor signal indicative heart sounds. The cardiac sensing circuit senses at least one cardiac signal indicative of cardiac electrical events. The gating module generates heart sound detection windows each timed for detection of one of selected heart sounds based on a time of occurrence of one of selected cardiac electrical events. The heart sound detector detects the selected heart sounds. The measurement module generates parameter values related to the selected heart sounds. The therapy circuit delivers a therapy based on the parameter values.

This summary is intended not to limit the claimed subject matter, and the scope of the invention is defined by attached claims and their equivalents.

BRIEF DESCRIPTION OF THE DRAWINGS

In the drawings, which are not necessarily drawn to scale, like numerals describe similar components throughout the several views. The drawings illustrate generally, by way of example, but not by way of limitation, various embodiments discussed in the present document.

DETAILED DESCRIPTION

Figure 1:
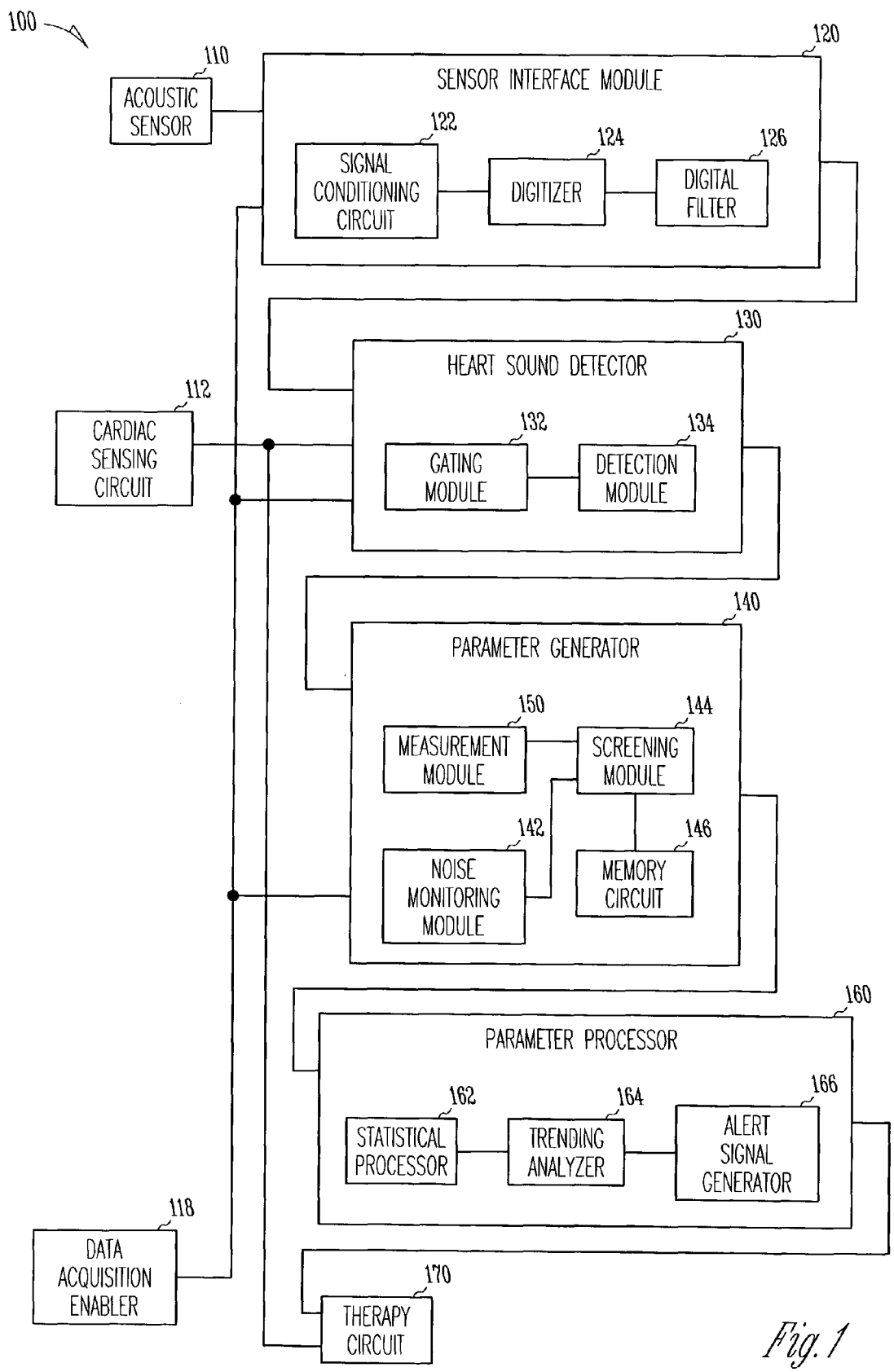
FIG. 1 is a block diagram illustrating an embodiment of a heart-sound based hemodynamics monitoring and therapy control system.

In the following detailed description, reference is made to the accompanying drawings that form a part hereof, and in which is shown, by way of illustration, specific embodiments in which the invention may be practiced. These embodiments are described in sufficient detail to enable those skilled in the art to practice the invention, and it is to be understood that the embodiments may be combined, or that other embodiments may be utilized and that structural, logical and electrical changes may be made without departing from the scope of the present invention. The following detailed description is, therefore, not to be taken in a limiting sense, and the scope of the present invention is defined by the appended claims and their equivalents.

This document discusses, among other things, a cardiac rhythm management system monitoring heart sounds indicative of a heart's mechanical events related to the heart's pumping functions and hemodynamic performance to allow, among other things, diagnosis of cardiac conditions and selection of therapies treating the cardiac conditions. The cardiac rhythm management systems include systems having, for example, pacemakers, cardioverter/defibrillators, pacemaker/defibrillators, and cardiac resynchronization therapy (CRT) devices. One specific example of a cardiac rhythm management system that monitors and analyses heart sounds is described in co-pending, commonly assigned Siejko et al. U.S. patent application Ser. No. 10/307,896, entitled "PHONOCARDIOGRAPHIC IMAGE-BASED ATRIO-VENTRICULAR DELAY OPTIMIZATION," filed Dec. 12, 2002, which is hereby incorporated by reference in its entirety. However, it is to be understood that the present methods and apparatuses may be employed in other types of medical devices, including, but not being limited to, drug delivery systems and various types of cardiac monitoring devices.

Known and studied heart sounds include the "first heart sound" or S1, the "second heart sound" or S2, the "third heart sound" or S3, the "fourth heart sound" or S4, and their various sub-components. S1 is known to be indicative of, among other things, mitral valve closure, tricuspid valve closure, and aortic valve opening. S2 is known to be indicative of, among other things, aortic valve closure and pulmonary valve closure. S3 is known to be a ventricular diastolic filling sound often indicative of certain pathological conditions including heart failure. S4 is known to be a ventricular diastolic filling sound resulted from atrial contraction and is usually indicative of pathological conditions. The term "heart sound" hereinafter refers to any heart sound (e.g., S1) and any components thereof (e.g., M1 component of S1, indicative of Mitral valve closure).

Throughout this document, "heart sound" includes audible and inaudible mechanical vibrations caused by cardiac activity that can be sensed with an accelerometer. Accordingly, the scope of "acoustic energy" in this document extends to energies associated with such mechanical vibrations.

Throughout this document, "user" refers to a physician or other caregiver who examines and/or treats a patient using one or more of the methods and apparatuses reported in the present document. Unless noted otherwise, S1, S2, S3, and S4 refer to the first, second, third, and fourth heart sounds, respectively, as a heart sound type, or as one or more occurrences of the corresponding type heart sounds, depending on the context.

FIG. 1 is a block diagram illustrating an embodiment of a heart-sound based hemodynamics monitoring and therapy control system 100. System 100 includes, among other things, an acoustic sensor 110, a sensor interface module 120, a cardiac sensing circuit 112, a heart sound detector 130, a parameter generator 140, a data acquisition timer 118, a parameter processor 160, and a therapy circuit 170. In one embodiment, system 100 is a totally implantable system adapted to be implanted into a patient. In an alternative embodiment, system 100 is an external system that does not include any implantable component. In another alternative embodiment, system 100 includes both implantable and external components.

Acoustic sensor 110 senses an acoustic energy or mechanical vibration energy related to cardiac mechanical activities and converts the acoustic energy to an acoustic sensor signal indicative of heart sounds. The acoustic sensor signal is an electrical signal indicative of timing, strength, and frequency characteristics related to the heart sounds. Acoustic sensor 110 is disposed in a heart, or near the heart in a location where the acoustic energy related to the cardiac mechanical activities can be sensed. In one embodiment, acoustic sensor 110 includes an accelerometer disposed in or near a heart. In another embodiment, acoustic sensor 110 includes a microphone disposed in or near a heart.

Sensor interface module 120 has a signal input connected to the output of acoustic sensor 110 to receive the acoustic sensor signal. It processes the acoustic sensor signal to prepare for detection of selected type heart sounds. The selected type heart sounds are heart sounds selected for a purpose of monitoring a patient's hemodynamic performance indicated by the measurable characteristics of these heart sounds. In one specific embodiment, the selected type heart sounds includes S3 and S4, which are indicative of ventricular diastolic hemodynamic performance. Sensor interface module includes a signal conditioning circuit 122, a digitizer 124, and a digital filter 126. Signal conditioning circuit 122 receives the acoustic sensor signal as an analog signal from acoustic sensor 110, and performs initial conditioning of the acoustic sensor signal. In one embodiment, signal conditioning circuit 122 improves the signal-to-noise ratio of the acoustic sensor signal. It includes an amplifier and a filter to amplify the acoustic sensor signal while reducing the noise therein. In one embodiment, the filter is an analog filter that substantially reduces amplitudes of noises that are not within the frequency spectrum of the selected type heart sounds. In another embodiment, the filter substantially reduces amplitudes of noises as well as components of the acoustic sensor signal that are outside of the frequency range of the selected type heart sounds. Digitizer 124 digitizes the filtered acoustic sensor signal by sampling it at a predetermined rate. In one embodiment, the sampling rate is programmable and determined based on known frequency characteristics of the heart sounds to be detected. In one embodiment, digitizer 124 samples the acoustic sensor signal only during predetermined periods of time where the selected type heart sounds are most likely to be present. This saves electrical energy required for processing the acoustic sensor signal and/or allows a higher resolution of the digitized acoustic sensor signal without substantially increasing the electrical energy required for processing. Energy conservation is of particular importance when system 100 is a totally implantable system or includes implantable components. Digital filter 126 substantially reduces amplitudes for all components of the acoustic sensor signal except the selected type heart sounds, which are to be detected by heart sound detector 130, thereby enhancing the indications of the selected type heart sounds. In one embodiment, digital filter 126 includes a band-pass filter having cutoff frequencies determined based on the frequency spectrum of the selected type heart sounds. It is to be understood, however, that the cutoff frequencies are dependent on the purpose of detection and need not cover exactly the known spectrum of particular heart sounds. In one specific embodiment, digital filter 126 is band-pass filter having a low cutoff frequency in the range of 5 to 20 Hz and a high cutoff frequency in the range of 30 to 120 Hz selected for the purpose of detecting S3 and S4. One example of a suitable pass band for digital filter 126 for detection of S3 and S4 for monitoring ventricular diastolic hemodynamics includes a low cutoff frequency of 10 Hz and a high cutoff frequency of 60 Hz. In one specific embodiment, digital filter 126 is an envelope detector type filter. In one embodiment, digital filter 126 is a programmable digital filter in which at least one of the cutoff frequencies is programmable. This allows a dynamic selection of heart sounds for detection without a need for additional circuitry.

Cardiac sensing circuit 112 senses at least one cardiac signal indicative of cardiac electrical events that are needed for detection and measurements related to the heart sounds and/or their components. In one embodiment, the cardiac signal includes a surface ECG signal. In another embodiment, the cardiac signal includes an intracardiac ECG signal that is also referred to as an electrogram. Cardiac sensing circuit 112 includes a sensing amplifier to sense the cardiac signal, a cardiac events detector to detect the cardiac electrical events, and an event marker generator to label each detected cardiac electrical event with an event marker indicative of the timing and type of the detected cardiac electrical event. The detected electrical events include, by not limited to, selected atrial and ventricular contractions. The atrial and ventricular contractions include spontaneous contractions and artificially stimulated contractions.

Figure 2:
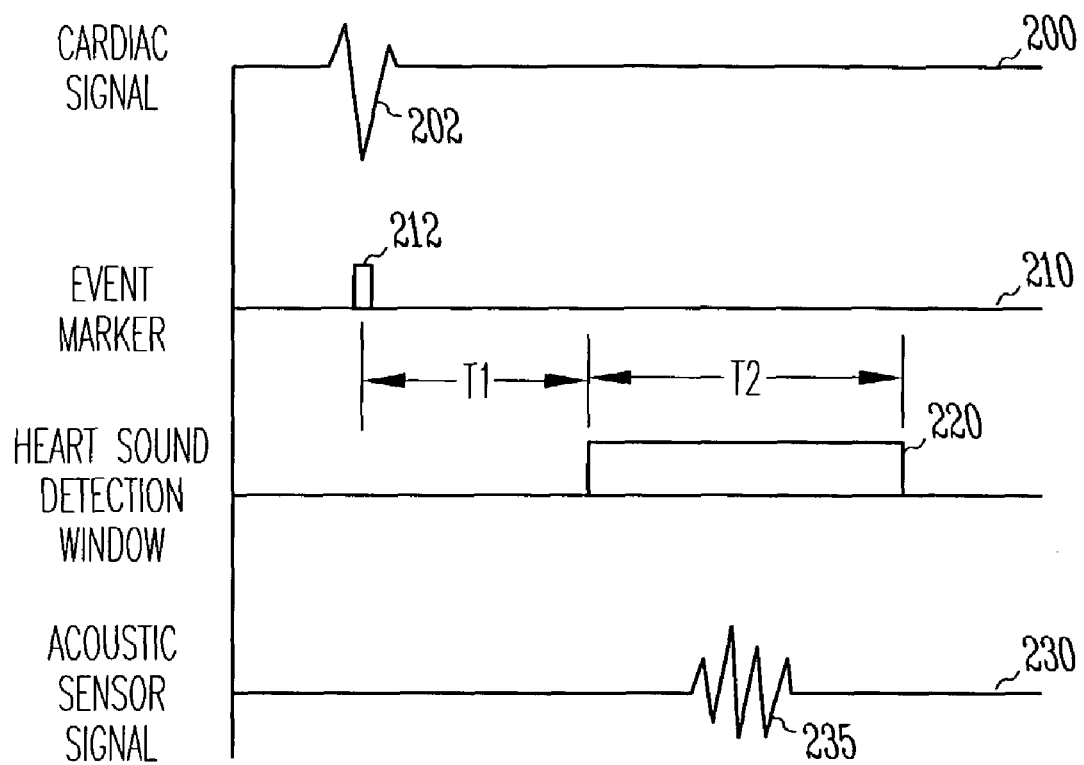
FIG. 2 is an illustration of an embodiment of a method for detecting selected heart sounds.

Heart sound detector 130 detects the selected type heart sounds. In one embodiment, heart sound detector 130 detects the selected type heart sounds based on the acoustic sensor signal. In another embodiment, heart sound detector 130 detects the selected type heart sounds based on the acoustic sensor signal and the cardiac signal sensed by cardiac sensing circuit 112. In one embodiment, heart sound detector includes a gating module 132 and a detection module 134. Gating module 132 receives the acoustic sensor signal from sensor interface module 120 and the cardiac signal from cardiac sensing circuit 112. In one embodiment, the cardiac signal received by gating module 132 includes event makers representing the detected cardiac electrical events that allow or facilitate detection of the selected type heart sounds. Gating module 132 generates heart sound detection windows each timed for detection of one of the selected type heart sounds based on a time of occurrence of one of cardiac electrical events. FIG. 2 illustrates, by way of example, but not by way of limitation, a heart sound detection window. As illustrated in FIG. 2, a cardiac signal 200 indicates a heart contraction 202. An event marker signal 210, which is a representation of cardiac signal 200, includes an event marker 212 representing heart contraction 202. An acoustic sensor signal 230, simultaneously recorded with cardiac signal 200, includes an indication of a heart sound 235. Based on available medical knowledge including statistical information available for an individual patient, heart sound 235 is substantially probable to occur within a time period T2 which starts after a time period T1 triggered by event marker 212 representing heart contraction 202. Thus, gating module 132 generates a heart sound detection window having a duration of T2 at the end of T1 following each heart contraction used for detection of the selected type heart sounds. In another embodiment, another heart sound (of a different type than the selected type) substitutes heart contraction 202 to trigger T1, and gating module 132 generates the heart sound detection window T2 at the end of T1 following each heart sound used for detection of the selected type heart sounds. In one embodiment, the heart sound detection windows are used to conserve energy and/or computational resources of system 100 by limiting the need for detection and subsequent computations to periods within the heart sound detection windows. In another embodiment, it is difficult or practically impossible to differentiate one type of the heart sounds from another by amplitude or frequency spectrum. This necessitates a method of detection that is not based on the amplitude or frequency spectrum of the selected type heart sounds. One feasible method includes the use one or more heart sound detection windows each corresponding to one or more types of heart sounds, thus allowing detections of heart sounds based on their predicted ranges of time of occurrence. Durations of the windows are determined based on an empirical study on the timing of each type of heart sounds relative to a type of cardiac. Heart sound detector 134 detects the selected type heart sounds. In one embodiment, heart sound detector 134 detects the selected type heart sounds within the one or more heart sound detection windows. In one embodiment, heart sound detector 134 includes one or more comparators to detect the selected type heart sounds by comparing the amplitude of the acoustic sensor signal during the one or more heart sound detection windows with one or more predetermined detection thresholds.

Figure 3:
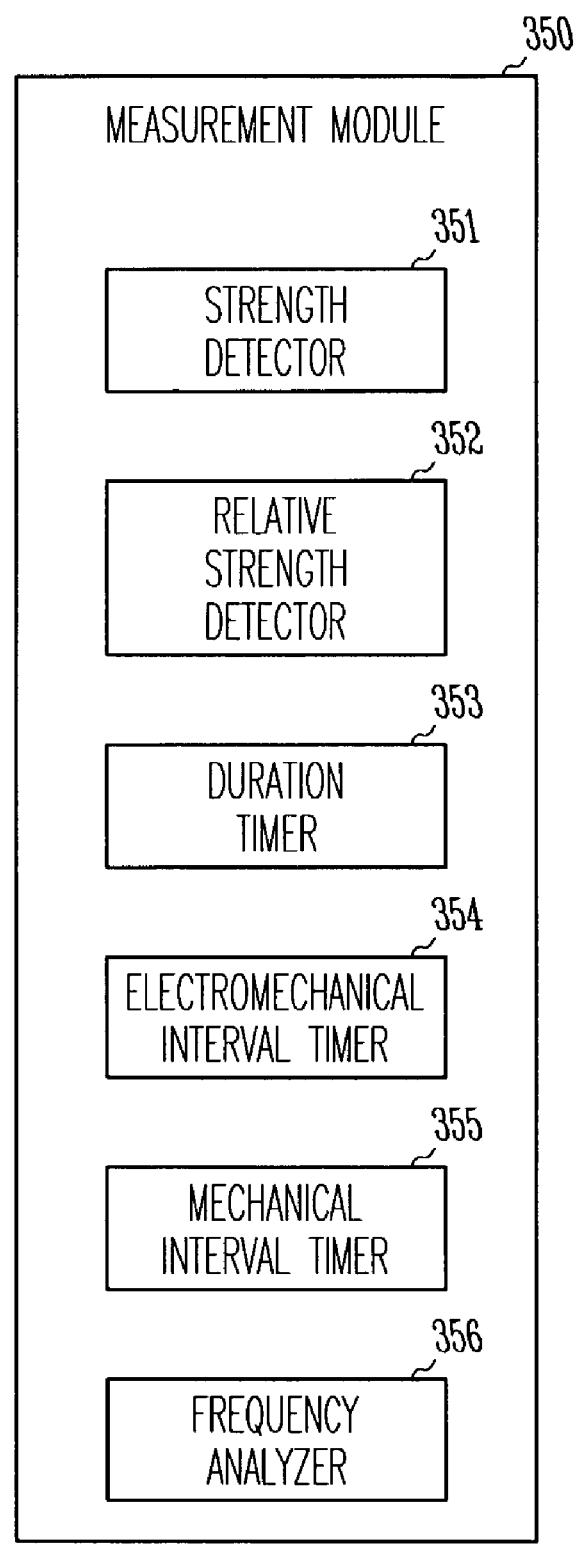
FIG. 3 is a block diagram illustrating an embodiment of a measurement module of the system of FIG. 1.

Following the detections of the selected type heart sounds by heart sound detector 130, parameter generator 140 makes measurements to generate parameter values of at least one predetermined parameter related to the detected heart sounds. In one embodiment, such a parameter value is measured from one detected heart sound. In another embodiment, the parameter value is calculated based on measurement of several detected heart sounds of the same type. The parameter values indicate the patient's hemodynamic performance, either directly or after further processing as discussed below. Parameter generator 140 includes a measurement module 150 to make measurements on the acoustic sensor signal. The measurements are timed with the detections of the selected type heart sounds. In one embodiment, measurement module 150 receives the acoustic sensor signal from heart sound detector 130 and the cardiac signal from cardiac sensing circuit 112. FIG. 3 is a block diagram that illustrates, by way of example, but not by way of limitation, components of measurement module 150. As illustrated in FIG. 3, measurement module 150 includes a strength detector 351, a relative strength detector 352, a duration timer 353, an electro-mechanical interval timer 354, a mechanical interval timer 355, and a frequency analyzer 356. Strength detector 351 measures amplitudes each associated with a detected heart sound. Relative strength detector 352 determines differences each between amplitudes associated with two detected heart sounds. Duration timer 353 measures durations each associated with a detected heart sound. Electromechanical interval timer 354 measures electro-mechanical time intervals each between a detected heart sound and a cardiac electrical event detected from the cardiac signal. Mechanical interval time 355 measures mechanical time intervals each between two detected heart sounds. Frequency analyzer 356 computes fundamental and/or harmonic frequencies each associated with a detected heart sound. In one embodiment, measurement module 150 calculate one or more parameter values each based on several values of a predetermined parameter measured by one of the components of measurement module 150. In one specific embodiment, measurement module 150 calculates the one or more parameter values each being an average of the several values of the predetermined parameter. Because of the nature and property of the acoustic sensor, the parameter values output from measurement module 150 may includes those affected by background interference. For example, when the acoustic sensor is an accelerometer, the acoustic sensor signal may indicate a patient's physical activities in addition to the heart sounds. When the acoustic sensor is a microphone, the acoustic sensor signal may indicate talking and other environment sounds in addition to the heart sounds. Thus, in one embodiment, parameter generator 140 includes a screening module 144 to exclude parameter values resulted from measurements performed when a background noise level exceeds a predetermined threshold. In one embodiment, a noise monitoring module 142 measures the background noise level. In one specific embodiment, noise monitoring module 142 includes an activity sensor that senses a patient's physical activities and an activity sensor interface module to convert the physical activities to the background noise level. In another specific embodiment, noise monitoring module includes a further sensor interface module coupled to acoustic sensor 110, which senses the patient's physical activities in addition to the acoustic energy related to the patient's cardiac mechanical activities. When acoustic sensor 110 includes an accelerometer, the further sensor interface module includes an activity level detector to produce the background noise level signal indicative of the patient's physical activities. The activity level as indicated by the acoustic sensor signal has a distinctively higher amplitude than the heart sounds. Thus, the activity level detector distinguishes the patient's physical activities from the heart sounds by using a predetermined activity level threshold. In one embodiment, parameter generator 140 includes a memory circuit 146 to store the parameter values generated by measurement module 150. In another embodiment, memory 146 stores only parameters screened by screening module 144.

Data acquisition enabler 118 controls the timing of overall data acquisition by timing the enablement of selected system components including at least one or more of acoustic sensor 110, sensor interface module 120, cardiac sensing circuit 112, heart sound detector 130, and parameter generator 140. In one embodiment, data acquisition enabler 118 enables the selected system components in response to an external command, such as given by the user. In another embodiment, data acquisition enabler 118 includes a data acquisition timer to enable the selected system components on a predetermined schedule. In one specific embodiment, the data acquisition timer enables the selected system components on a predetermined periodic basis. In another specific embodiment, if parameter generator 140 is unable to generate required parameter values on the predetermined schedule, for example, because the background noises exceeds the predetermined level when the selected system components are enabled, data acquisition enabler 118 modifies the predetermined schedule by introducing at least one delay to ensure that all the desired parameter values are obtained.

Parameter processor 160 processes the parameter values received from parameter generator 140. In one embodiment, parameter processor 160 includes a statistical processor 162, a trending analyzer 164, and an alert signal generator 166. Statistical processor 162 analyzes the parameter values generated by parameter generator 140 for a predetermined period of time. Trending analyzer 164 produces at least one trend related to the selected type heart sounds. The trend is a hemodynamic performance trend indicative of one or more cardiac conditions. In one embodiment, the trend is a plot of parameter values of one selected parameter related to the detected heart sounds over a predetermined period of time. In another embodiment, the trend is a plot of values derived for the parameter values as a result of the statistical process over the predetermined period of time. Alert signal generator 166 generates an alert signal indicative of a presence of the one or more cardiac conditions indicated by the at least one trend. In one embodiment, alert signal generator 166 includes a comparator. The comparator has a first input to receive the at least one trend, a second input representative of a predetermined threshold level, and an output indicative of the presence of the one or more clinical conditions when the at least one trend exceeds the predetermined threshold level. In one further embodiment, alert signal generator 166 includes a threshold generator that generates an adaptive threshold level based on at least one previously produced trend, such that the predetermined threshold is dynamically adjustable based on the patient's changing cardiac conditions.

Therapy circuit 170 includes, by way of example, but not by way of limitation, one or more of a pacing circuit, a defibrillation circuit, a cardiac resynchronization circuit, and a drug delivery circuit. It includes a therapy controller to execute a predetermined therapy algorithm that times therapy deliveries based on the processed cardiac signal and acoustic sensor signal. In one embodiment, the therapy controller receives at least one of selected parameter values generated by parameter generator 140, the at least one trend generated by trending analyzer 164, and the alert signal generated by alert signal generator 166, based on which it produces or adjusts one or more therapy parameters.

Figure 4:
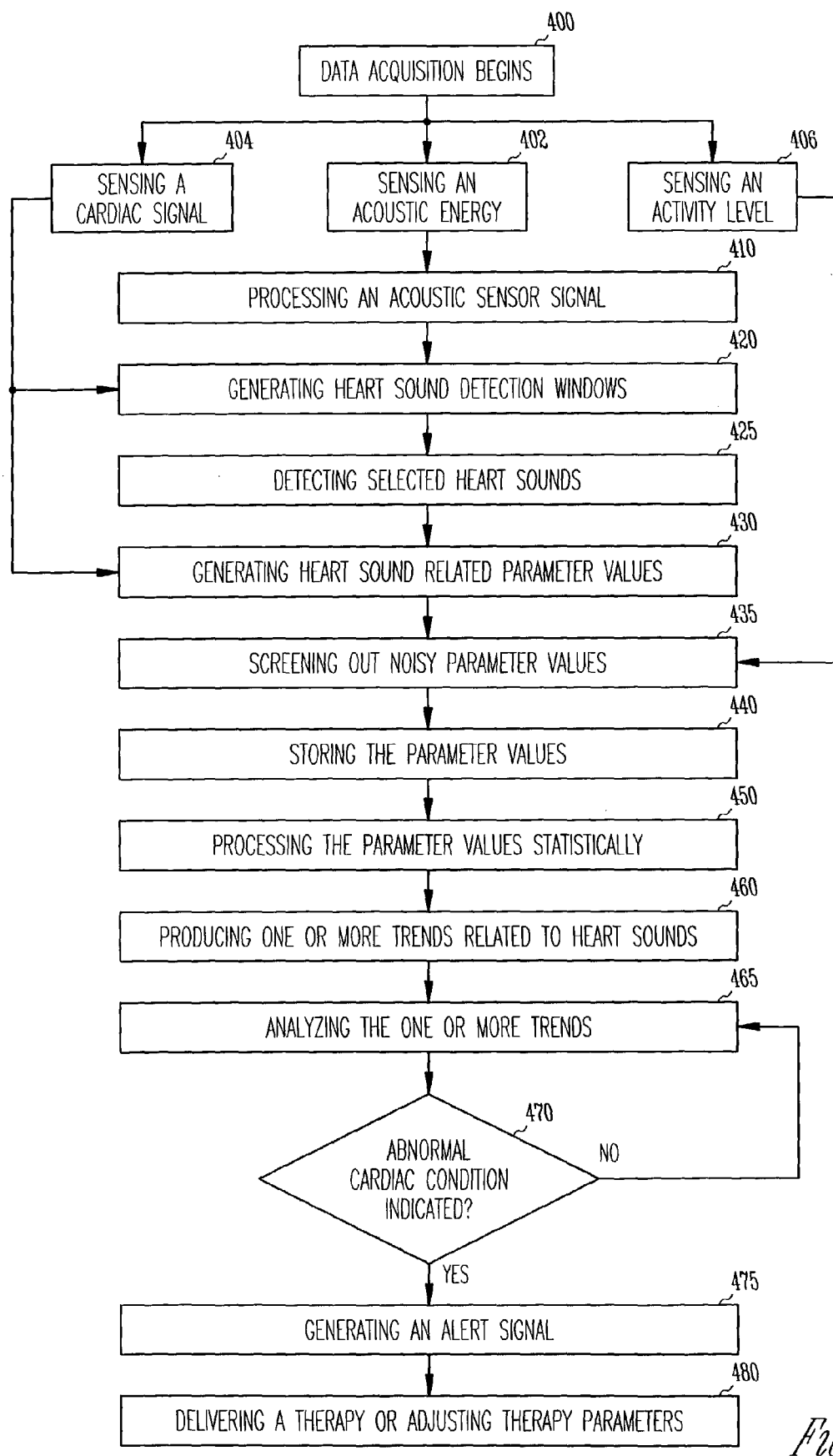
FIG. 4 is a flow chart illustrating an embodiment of a method for hemodynamics monitoring and therapy control using the system of FIG. 1.

FIG. 4 is a flow chart illustrating an embodiment of a method for hemodynamics monitoring and therapy control using system 100. At 400, data acquisition for the hemodynamics monitoring and therapy control begins. In one embodiment, the data acquisition begins as system 100 is activated. In one embodiment, the data acquisition begins in response to a user command. In another embodiment, the data acquisition begins at a predetermined time or upon a predetermined triggering event. In one embodiment, the date acquisition lasts for a predetermined duration after it begins. In one specific embodiment, the data acquisition begins on a predetermined periodic basis and lasts for a predetermined duration.

At 402, acoustic sensor 110 senses the acoustic energy related to cardiac mechanical activities and converts the acoustic energy to an acoustic sensor signal indicative heart sounds. In one embodiment, acoustic sensor 110 senses an acceleration indicative of the acoustic energy.

At 410, sensor interface module 410 processes the acoustic sensor signal to prepare for heart sound detection. In one embodiment, the acoustic sensor signal is amplified and filtered to increase its signal-to-noise ratio. Then, the acoustic sensor signal is digitized to the form of binary data. The digitized acoustic sensor signal is filtered to enhance indications of the selected type heart sounds. In one embodiment, the digitized acoustic sensor signal is filtered with at least one cutoff frequency determined based on the frequency spectrum of the selected type heart sounds.

At 420, heart sound detector 130 generates heart sound detection windows each timed for detecting one of the selected type heart sounds. The heart sound detection windows are each triggered by one of selected cardiac electrical events detected from the cardiac signal sensed at 404. In one embodiment, the selected cardiac electrical events include at least one of spontaneous or artificially stimulated atrial and ventricular contractions. In one embodiment, the selected cardiac electrical events are each represented by a predetermined event marker. In one specific embodiment, At 425, the selected type heart sounds are detected. In one embodiment, each of the selected type heart sounds is detected when the amplitude of the acoustic sensor signal exceeds a predetermined threshold level.

At 430, parameter generator 140 generates the parameter values of at least one parameter related to the detected heart sounds based on the acoustic sensor signal produced at 400 and/or the cardiac signal sensed at 404. Such parameter values include, by way of example, but not by way of limitation, one or more of (i) an amplitude associated with one or one selected type of the selected type heart sounds; (ii) a relative strength being differences between amplitudes associated with two or two selected types of the selected type heart sounds; (iii) a duration associated with one or one selected type of the selected type heart sounds; (iv) an electro-mechanical time intervals between one or one selected type of the selected type heart sounds and one or one type of selected type cardiac electrical events; (v) a mechanical time interval between two or two selected types of the selected type heart sounds; and (vi) a fundamental or harmonic frequency associated with one or one selected type of the selected type heart sounds. In one embodiment, parameter values related to S3 and/or S4 are measured and/or calculated for the purpose of monitoring ventricular diastolic hemodynamic performance. The parameter values of one or more of the following parameters are generated: (i) peak amplitude of S3; (ii) time of onset of S3 relative to onset of S2; (iii) duration of S3; (iv) fundamental frequency if S3; (v) time of occurrence of S3 relative to the subsequently adjacent atrial contraction; (vi) peak amplitude of S4; (vii) time interval between atrial contraction and the subsequently adjacent S4; (viii) fundamental frequency of S4; (ix) duration of S4; (x) time of occurrence of S4 relative to the subsequently adjacent ventricular contraction; and (xi) amplitude of S4 relative to amplitude of S3. In one embodiment, parameter generator 140 screens out noisy values of the parameter values measured at 435. Such noisy values include parameter values measured when the background noise level exceeds a predetermined threshold. In one embodiment, the patient's physical activities are sensed at 406 to produce an activity level signal indicative of the background noise level. In one specific embodiment, the activity level signal is derived from the same acoustic sensor signal from which the selected type heart sounds are detected. This is possible because the patient's physical activities are typically indicated with amplitudes that are distinctively higher than the amplitudes of the selected type heart sounds.

At 440, the parameter values are stored in memory circuit 146 or other storage medium. In one embodiment, system 100 uses the parameter values directly to control delivery of at least one therapy with at least one therapy parameter being a function of the parameter values. In another embodiment, the parameter values are further processed and analyzed by system 100 for monitoring, diagnosis, and/or therapy control purposes. In yet another embodiment, the stored parameter values are transferred to another system, such as a computer separated from system 100, for further processing and/or analysis.

At 450, parameter processor 160 statistically processes the parameter values. The statistical process includes analyzing the parameter values of the at least one parameter related to the detected heart sounds in relation to historical values of that parameter measured during a predetermined period of time. The outcome of the statistical process reveals changes in cardiac conditions reflected in the characteristics of the selected type heart sounds. In one embodiment, the outcome of the statistical process reveals changes in ventricular diastolic filling patterns during the predetermined period of time. In one specific embodiment, the predetermined period of time ranges from 1 day to 3 months.

At 460, parameter processor 160 produces at least one hemodynamic performance trend related to the selected type heart sounds. In one embodiment, parameter processor 160 produces the at least one trend based on the outcome of the statistical analysis. In one embodiment, one or more trends quantitatively present one or more ventricular diastolic filling pattern changes during a predetermined duration. In one embodiment, parameter processor 160 plots the parameter values of the at least one parameter related to the detected heart sounds versus time. In another embodiment, parameter processor 160 statistically processes the parameter values of the at least one parameter related to the detected heart sounds and plots the result. At 465, the one or more trends are analyzed for indication of cardiac conditions. In one embodiment, the values of each trend are compared to a predetermined threshold level, and a predefined cardiac condition is indicated when any value exceeds the predetermined threshold level. In one embodiment, the predetermined threshold level is determined based on at least one previously produced trend.

At 475, an alert signal is generated when a cardiac condition is indicated by the at least one hemodynamic performance trend at 470. The alert signal notifies the user of the cardiac condition that may need medical attention. In one embodiment, the cardiac condition requires delivery of a therapy. In another embodiment, the alert signal indicates a need for changing one or more therapy parameters.

In one embodiment, a therapy is delivered in response to the alert signal at 480. The therapy includes one or more of, for example, a pacing therapy, a defibrillation therapy, a cardiac resynchronization therapy, any other electrical stimulation therapy, and a drug therapy. The type of the therapy as therapy parameters are determined based on the at least one trend and/or selected values of the at least one parameter related to the detected heart sounds. In one specific embodiment, therapy circuit 170 delivers the therapy. In another embodiment, one or more therapy parameters are adjusted in response to the alert signal, and the new therapy parameters are determined based on the at least one trend and/or the selected values of the at least one parameter related to the detected heart sounds. In an alternative embodiment, the therapy delivery or the therapy parameter adjustments are not dependent on the alert signal. The at least one trend and/or the selected values of the at least one parameter related to the detected heart sounds directly determine the need for the therapy delivery or the therapy parameter adjustments.

Many embodiments combining the present method with available medical knowledge will be apparent to those of skill in the art. In one example, the fundamental frequency (also referred to as the pitch) of S3 is correlated to the stiffness of the left ventricular wall during the rapid filling phase of diastole. The wall stiffness is proportional to diastolic pressure in the left ventricle and to the thickness of the left ventricular wall. Therefore, an increase in the pitch of S3 is used to indicate one or more of an elevated left ventricular filling pressure and a thickened left ventricular wall. The elevation of the left ventricular filling pressure and/or the increase of the left ventricular wall thickness may reach a degree, represented by predetermined thresholds of S3 fundamental frequency, that requires an application of adjustment of a therapy. In another example, the amplitude of S3 is directly related to the rate of deceleration of blood flow into the left ventricle during the rapid filling phase of diastole. An increase in amplitude of S3 can be used to indicate an elevation of left atrial filling pressure, an increase in stiffness of the left ventricle, or both, which represent a restrictive filling pattern associated with heart failure. Therefore, the trend of S3 amplitude is useful in monitoring cardiac mechanical properties related to heart failure. In yet another example, the elevated filling pressures cause pulmonary edema. Thus, a physician determines the need of a drug therapy to relieve the elevated pressures based on one or more trends of parameters related to S3. These are a few examples, among many possible embodiments, illustrating how system 100 is used. In general, trends of any of the measured parameter values can be used individually, jointly, and/or in combination with other trends related to cardiac functions.

Figure 5:
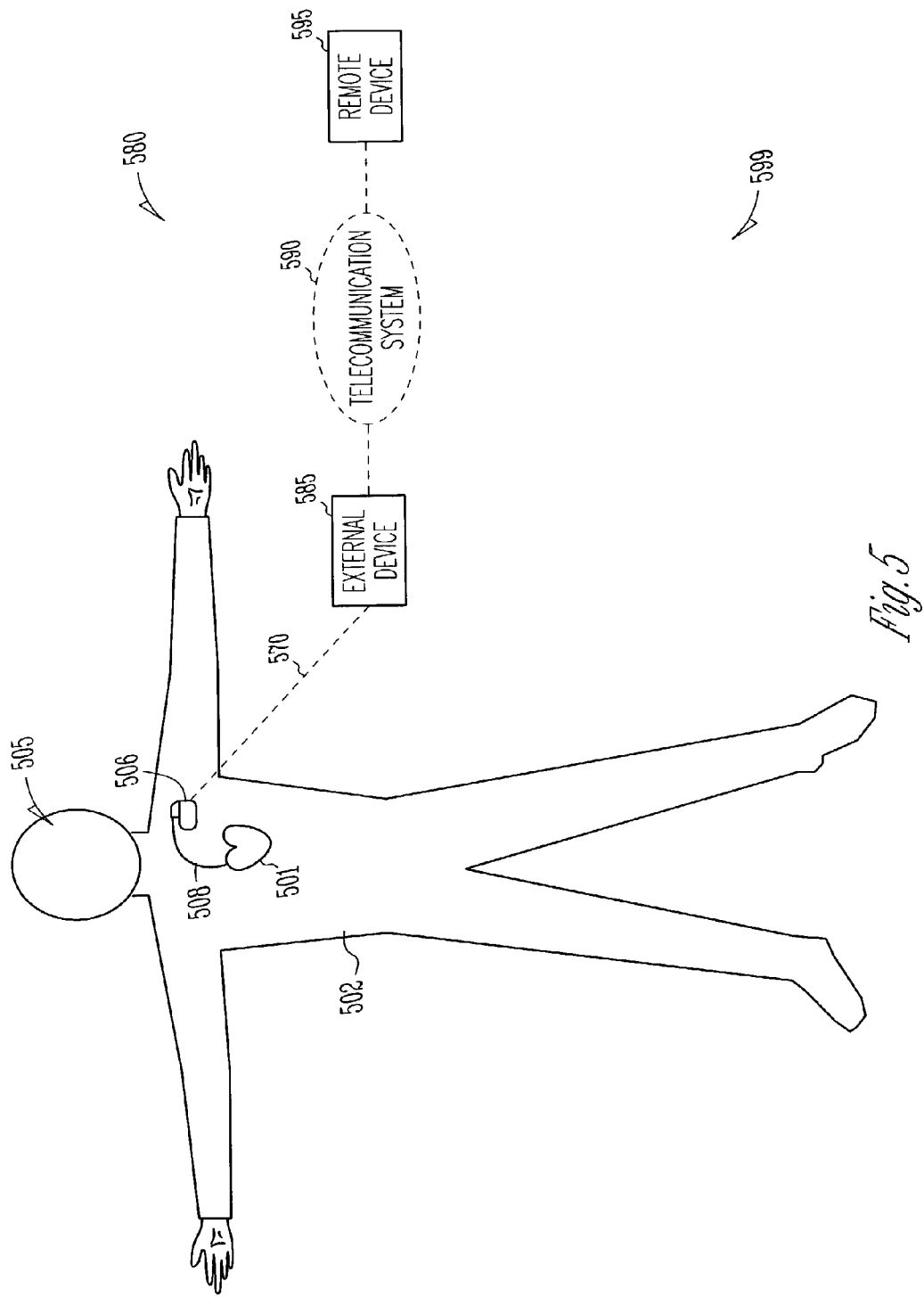
FIG. 5 is an illustration of an embodiment of portions of a cardiac rhythm management system incorporating heart-sound based hemodynamics monitoring and therapy control and portions of an environment in which it is used.

FIG. 5 is an illustration of an embodiment of portions of a cardiac rhythm management system 599 and portions of an environment in which it is used. System 599 incorporates a heart-sound based hemodynamics monitoring and therapy control system such as system 100. In one embodiment, cardiac rhythm management system 599 includes an implanted system 505, an external system 580, and a telemetry link 570 providing for communication between implanted system 505 and external system 580. Implanted system 505 includes an implanted device 506 and a lead system 508. Implanted device 506 is implanted within a patient's body 502 and coupled to the patient's heart 501 via lead system 508. Examples of implanted device 506 include pacemakers, cardioverter/defibrillators, pacemaker/defibrillators, cardiac resynchronization devices, and drug delivery devices. External system 580 is a patient management system including an external device 585 in proximity of implanted device 502, a remote device 595 in a relatively distant location, and a telecommunication system 590 linking external device 585 and remote device 595. An example of such a patient management system is discussed in Hatlestad et al., "ADVANCED PATIENT MANAGEMENT FOR DEFINING, IDENTIFYING AND USING PREDETERMINED HEALTH-RELATED EVENTS," application Ser. No. 10/323,604, filed on Dec. 18, 2002, assigned to Cardiac Pacemakers, Inc., the specification of which is incorporated herein by reference in its entirety. In one embodiment, telemetry link 570 is an inductive telemetry link. In an alternative embodiment, telemetry link 570 is a far-field radio-frequency telemetry link. In one embodiment, telemetry link 570 provides for data transmission from implanted device 506 to external device 585. This may include, for example, transmitting real-time physiological data acquired by implanted device 506, extracting physiological data acquired by and stored in implanted device 506, extracting therapy history data stored in implanted device 506, and extracting data indicating an operational status of implanted device 506 (e.g., battery status and lead impedance). In a further embodiment, telemetry link 570 provides for data transmission from external device 585 to implanted device 506. This may include, for example, programming implanted device 506 to acquire physiological data, programming implanted device 506 to perform at least one self-diagnostic test (such as for a device operational status), and programming implanted device 506 to deliver at least one therapy.

In one embodiment, programming implanted device 506 includes sending therapy parameters to implantable device 506. The therapy parameters provide an improved hemodynamic performance for a patient by delivering cardiac pacing pulses to the patient's heart. In one embodiment, the therapy parameters providing for the improved hemodynamic performance are determined by monitoring one or more ventricular diastolic hemodynamics as indicated by parameters related to heart sounds such as S3 and S4. Such parameters indicate the heart's mechanical activities and electro-mechanical association. In one specific embodiment, the acquisition of values of such parameters, the processing of the parameter values, and the subsequent determination of the therapy parameters are performed by system 100, as discussed above with reference to FIGS. 1-3.

Figure 6:
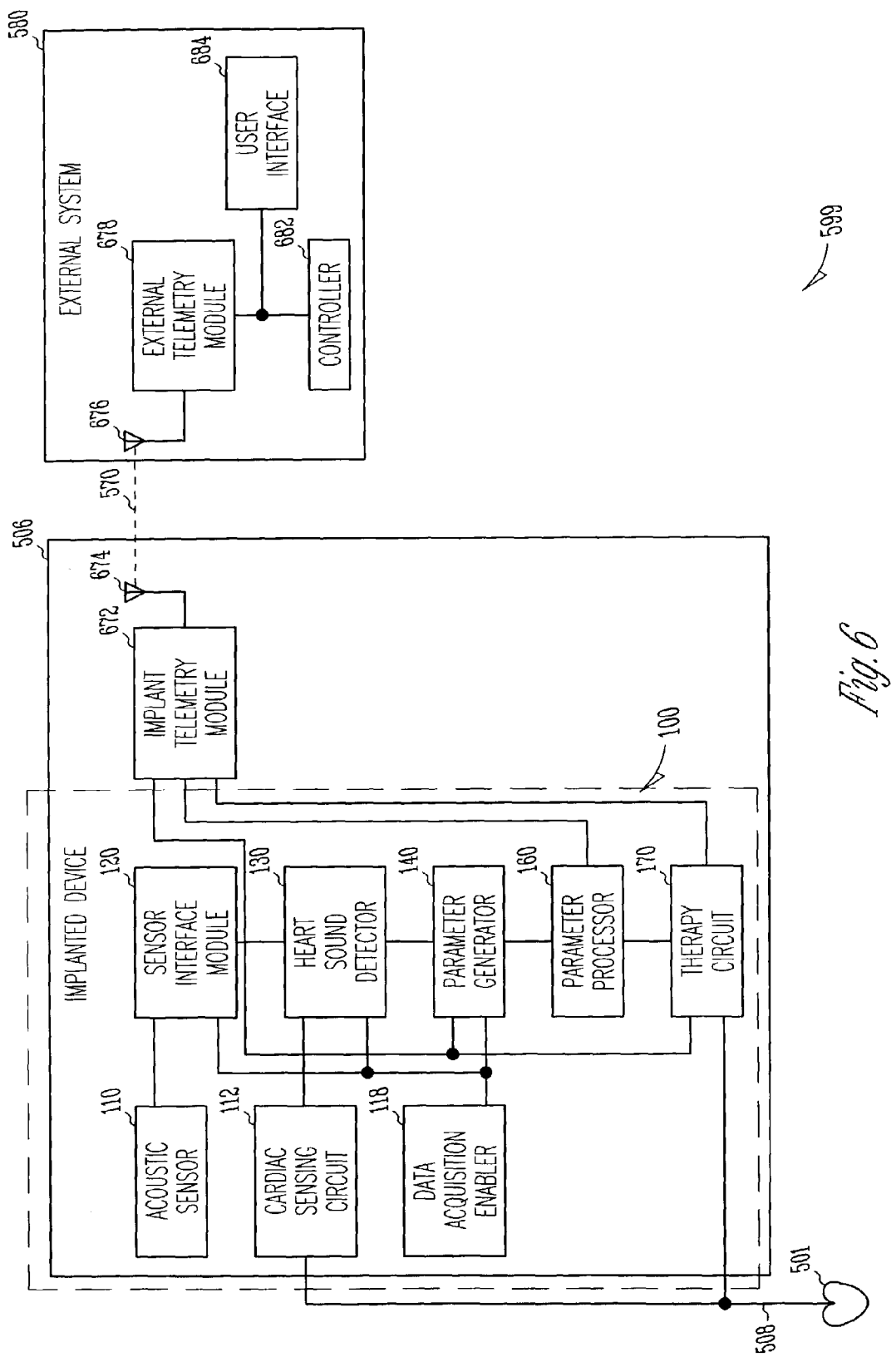
FIG. 6 is a block diagram illustrating a specific embodiment of portions of the cardiac rhythm management system of FIG. 5.

FIG. 6 is a block diagram illustrating a specific embodiment of portions of cardiac rhythm management system 599. In this embodiment, system 100 is substantially included within implanted device 506. System 100 includes, as discussed above with reference to FIG. 1, acoustic sensor 110, sensor interface module 120, cardiac sensing circuit 112, heart sound detector 130, parameter generator 140, data acquisition timer 118, parameter processor 160, and therapy circuit 170. Implanted device 506 also includes, among other things, an implant telemetry module 672 and an implant antenna 674 to provide implanted device 506 with telemetry capability allowing it to communicate with external system 580 via telemetry link 570. In one embodiment, therapy circuit 170 includes a therapy controller that executes a predetermined therapy control algorithm to determine whether to deliver a therapy or adjust one or more therapy parameters based on the one or more of the heart sound-related parameter values generated by parameter generator 140 and trends and alert signal generated by parameter processor 160.

External system 580 includes, among other things, an external antenna 676, an external telemetry module 678, a controller 682, and a user interface 684. In one embodiment, external telemetry module 678 and external antenna 676 are included in external device 585 to provide external system 580 with capability of communicating with implanted device 506 through telemetry link 570 and external device 585. Controller 682 controls telemetry operation of external system 580, processes signals received from implanted device 506 for presentation on user interface 684, and processes user commands entered through user interface 684 for transmission to implanted device 506. In one embodiment, one or more of the heart-sound related parameter values, trends, and alert signal, as discussed above, are acquired by system 100 and telemetered to external system 580 via telemetry link 570. Controller 682 executes a predetermined therapy control algorithm to determine whether to deliver a therapy or adjust one or more therapy parameters based on the one or more of the heart sound-related parameter values, trends, and alert signal.

In one embodiment, system 100 is completely within a hermetically sealed can that houses at least portions of implanted device 506. Housing acoustic sensor 110 in the can has the advantage of minimizing the background noise associated with physical movements of the sensor, especially when acoustic sensor 110 includes an accelerometer. In another embodiment, acoustic sensor 110 is attached to a lead of lead system 508. This allows disposition of acoustic sensor 110 in or near heart 501 such that it is near the mechanical activities being the sources of the heart sounds of interest.

To include substantially the whole system 100 within implanted device 506 provides for the advantage of a self-contained implantable cardiac rhythm management system incorporating heart-sound based therapy control. In one embodiment, the heart-sound based therapy control using system 100 is able to function without telemetry link 570, for example, when the patient is outside the range of the telemetry communication. Implanted device 506 determines, without the intervention of the user or controller 682, whether to deliver a therapy or adjust one or more therapy parameters based on the one or more of the parameter values, trends, and alert signal generated within itself by system 100.

Figure 7:
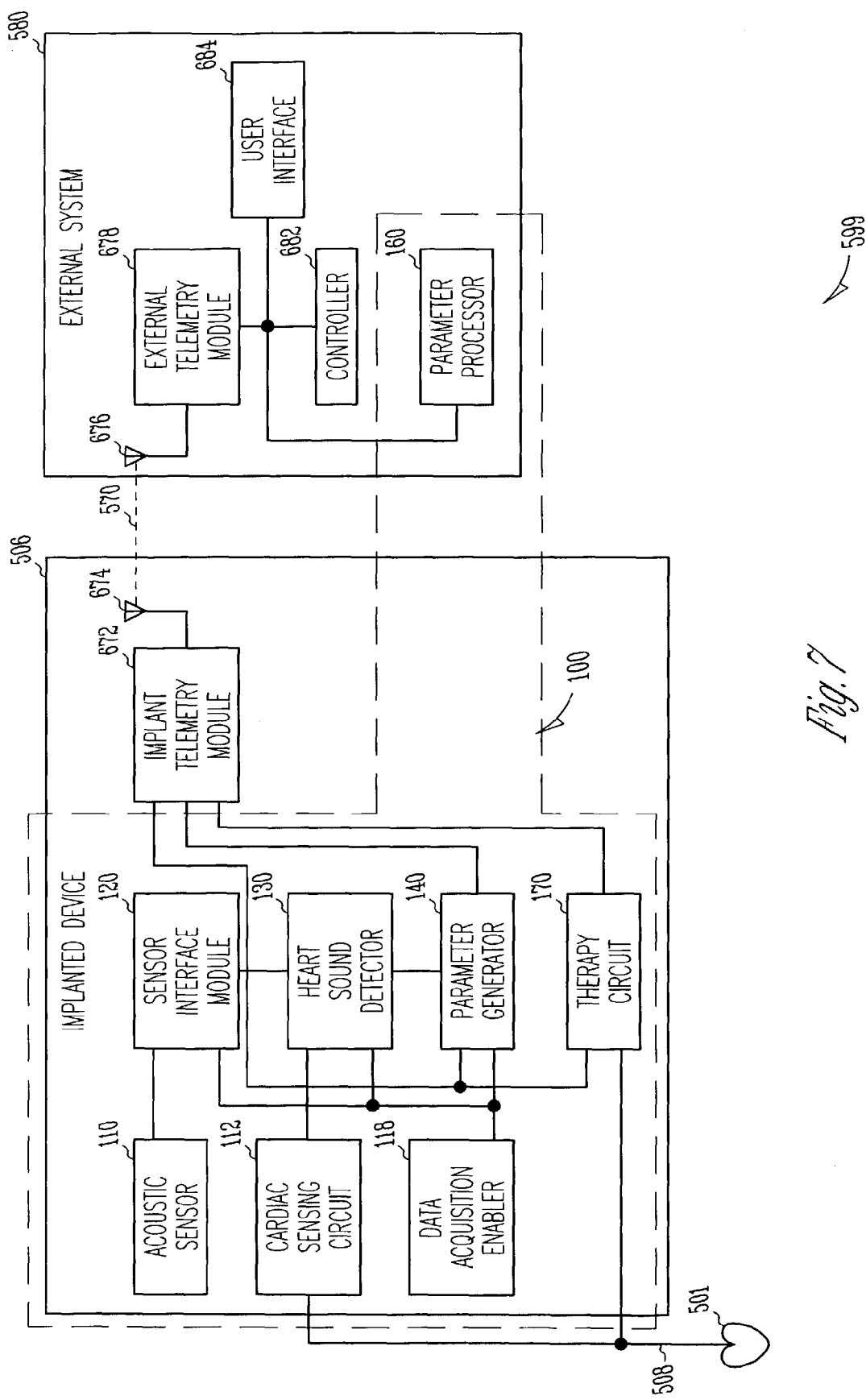
FIG. 7 is a block diagram illustrating another specific embodiment of portions of the cardiac rhythm management system of FIG. 5.

FIG. 7 is a block diagram illustrating another specific embodiment of portions of cardiac rhythm management system 599. In this embodiment, system 100 is partially included within implantable device 506 and partially included in external system 580. In one specific embodiment, parameter processor 160 is within external system 580, and the remaining components of system 100 are within implanted device 506. Parameter values generated by parameter generator 140 are telemetered to external system 580 via telemetry link 570 for further processing by parameter processor 160. In one embodiment, parameter processor 160 is included in external device 585. In an alternative embodiment, parameter processor 160 is included in remote device 595.

In one embodiment, the parameter values are telemetered as they are generated. In another embodiment, parameter values are first stored in memory circuit 146. Data acquisition enabler 118 times transmission of the parameter values in response to a command from external device 580 or on a predetermined schedule.

To include parameter processor 160 in external system 580 avoids placing the demand of energy and circuit resources required by parameter processor 160 in implanted device 506, which is subject to design restraints including power and size limitations. The advantages also include the feasibility of updating parameter processing algorithms used by parameter processor 160 without the need of replacing implanted device 506.

It is to be understood that the above detailed description is intended to be illustrative, and not restrictive. For example, system 100 may be incorporated into any implanted or external medical device providing for ECG and heart sound monitoring. Other embodiments will be apparent to those of skill in the art upon reading and understanding the above description. The scope of the invention should, therefore, be determined with reference to the appended claims, along with the full scope of equivalents to which such claims are entitled.

What is claimed is:

1. A system adapted to be coupled to a patient, comprising:
an acoustic sensor including an accelerometer adapted to sense an acoustic energy and produce an acoustic sensor signal indicative of heart sounds of the patient and physical activities of the patient;
a signal conditioning circuit coupled to the acoustic sensor, the signal conditioning circuit adapted to filter the acoustic sensor signal to reduce noise in the acoustic sensor signal;
a cardiac sensing circuit to sense a cardiac signal indicative of cardiac electrical events;
a heart sound detector coupled to the signal conditioning circuit and the cardiac sensing circuit, the heart sound detector adapted to detect selected heart sounds based on the acoustic sensor signal and the cardiac signal, the selected heart sounds indicative of ventricular diastolic hemodynamic performance;
a parameter generator coupled to the heart sound detector, the parameter generator adapted to make measurements on the acoustic sensor signal timed using the detected selected heart sounds and generate values of at least one predetermined parameter related to the selected heart sounds using the measurements and including:
a noise monitoring module adapted to produce a background noise level using the acoustic sensor signal, the background noise level indicative of the physical activities of the patient; and
a screening module coupled to the noise monitoring module and adapted to exclude the values of the at least one predetermined parameter generated using the measurements made when the background noise level exceeds a predetermined level;
a processor coupled to the parameter generator, the processor adapted to perform a statistical process analyzing the values of the at least one predetermined parameter generated for a predetermined duration and produce at least one trend quantitatively presenting one or more ventricular diastolic filling pattern changes during the predetermined duration using an outcome of the statistical process;
a data acquisition enabler adapted to time data acquisition by enabling one or more system components according to a predetermined schedule, the one or more system components including one or more of the acoustic sensor, the cardiac sensing circuit, the heart sound detector, and the parameter generator; and
a therapy circuit communicatively coupled to the processor, the therapy circuit adapted to deliver at least one cardiac therapy with at least one therapy parameter determined based on the at least one trend.

2. The system of claim 1, further comprising a sensor interface module coupled between the acoustic sensor and the parameter generator, the sensor interface module including:
  a digitizer, coupled to the acoustic sensor, to digitize the acoustic sensor signal; and
  a band-pass filter having at least one programmable cutoff frequency, coupled to the digitizer, to enhance indications of the selected heart sounds in the digitized acoustic sensor signal.

3. The system of claim 2, wherein the band-pass filter includes an envelope-detector type filter having a low cutoff frequency in the range of 5 to 20 Hz and a high cutoff frequency in the range of 30 to 120 Hz.

4. The system of claim 1, wherein the cardiac sensing circuit comprises:
  a cardiac events detector, coupled to the sensing amplifier, to detect the cardiac electrical events; and
  an event marker generator, coupled to the cardiac events detector, to generate event markers representing selected events of the detected cardiac electrical events.

5. The system of claim 1, wherein the heart sound detector comprises a gating module coupled to the acoustic sensor and the cardiac sensing circuit, the gating module adapted to generate heart sound detection windows each timed for detection of one of the selected heart sounds based on a time of occurrence of one of selected cardiac electrical events.

6. The system of claim 5, wherein the parameter generator comprises a measurement module including at least one of:
  a strength detector adapted to measure amplitudes each associated with a selected type of the selected heart sounds;
  a relative strength detector adapted to determine differences each between amplitudes associated with two selected types of the selected heart sounds;
  a duration timer adapted to measure durations each associated with a selected type of the selected heart sounds;
  an electromechanical interval timer adapted to measure time intervals each between a selected type of the selected heart sounds and a selected type of the selected cardiac electrical events;
  a mechanical interval timer adapted to measure time intervals each between two selected types of the selected type heart sounds; and
  a frequency analyzer adapted to compute a fundamental frequency associated with a selected type of the selected heart sounds.

7. The system of claim 1, wherein the parameter generator further comprises a memory circuit, coupled to the screening module, to store screened values of the at least one predetermined parameter.

8. The system of claim 1, wherein the data acquisition enabler is adapted to time the data acquisition by enabling the one or more system components for a predetermined duration on a periodic basis.

9. The system of claim 1, further comprising an alert signal generator, coupled to the trending analyzer, the alert signal generator adapted to generate an alert signal indicative of a predetermined cardiac condition based an outcome of a trending analysis.

10. The system of claims 9, wherein the trending analyzer comprises a comparator including a first input representative of the at least one trend, a second input representative of a threshold level, and an output representative of the outcome of the trending analysis.

11. The system of claim 10, wherein the trending analyzer further comprises a threshold generator adapted to generate the threshold level based on the values of the at least one predetermined parameter measured during a second predetermined period of time.

12. The system of claim 1, wherein the data acquisition enabler is adapted to time the data acquisition by enabling the one or more system components in response to a user command.

13. The system of claim 1, wherein the therapy circuit comprises a drug delivery circuit.

14. The system of claim 1, comprising:
  an implantable device including at least the acoustic sensor, the cardiac sensing circuit, the heart sound detector a parameter generator coupled to the heart sound detector, the parameter generator, and the therapy circuit; and
  an external system communicatively coupled to the implanted device, the external system including the processor.

15. The system of claim 1, wherein the data acquisition enabler is adapted to modify the predetermined schedule in response to the background noise level exceeding the predetermined level when the one or more system components are enabled.

16. The system of claim 1, wherein the at least one predetermined parameter comprises differences each between amplitudes associated with two selected types of the selected heart sounds, and the parameter generator comprises a relative strength detector adapted to determine the differences each between the amplitudes associated with the two selected types of the selected heart sounds.

17. The system of claim 1, wherein the at least one predetermined parameter comprises a fundamental frequency associated with a selected type of the selected heart sounds, and the parameter generator comprises a frequency analyzer adapted to compute the fundamental frequency associated with the selected type of the selected heart sounds.

18. A method, comprising:
  sensing an acoustic energy to produce an acoustic sensor signal using an accelerometer, the acoustic signal indicative heart sounds of a patient and physical activities of the patient;
  amplifying and filtering the acoustic sensor signal to increase a signal-to-noise ratio of the acoustic sensor signal;
  sensing at least one cardiac signal indicative of cardiac electrical events;
  detecting selected heart sounds indicative of ventricular diastolic hemodynamic performance;
  measuring the acoustic sensor signal;
  timing the measuring the acoustic sensor signal using the detected selected heart sounds;
  generating values of at least one predetermined parameter related to the selected heart sounds and selected cardiac electrical events using a result of the measuring the acoustic sensor signal;
  producing a background noise level using the acoustic sensor signal, the background noise level indicative of the physical activities of the patient;
  excluding the values of the at least one predetermined parameter generated using the acoustic sensor signal measured when the background noise level exceeds a predetermined level;
  performing a statistical process analyzing selected values of the at least one predetermined parameter, the selected values associated with one or more types of the selected heart sounds detected during a first predetermined period of time, the one or more types of the selected heart sounds indicative of ventricular diastolic hemodynamic performance;

producing at least one trend quantitatively presenting one or more ventricular diastolic filling pattern changes during the predetermined period of time using an outcome of the statistical process; and delivering at least one therapy with at least one parameter determined based on the at least one trend.

19. The method of claim 18, further comprising:
determining at least one cutoff frequency facilitating detection of third heart sounds (S3) and fourth heart sounds (S4);
programming the at least one cutoff frequency to a filter; and
filtering the acoustic sensor signal to enhance indications of S3 and S4 in the acoustic sensor signal.

20. The method of claim 18, wherein sensing at least one cardiac signal comprises:
detecting the cardiac electrical events including atrial and ventricular contractions; and
generating event markers representative of selected events of the detected cardiac electrical events.

21. The method of claim 18, wherein detecting the selected heart sounds comprises generating heart sound detection windows each timed for detecting one of the selected heart sounds based on a time of occurrence of one of the selected cardiac electrical events.

22. The method of claim 21, wherein generating values of at least one predetermined parameter comprises generating at least one of:
amplitudes each associated with a selected type of the selected heart sounds;
relative strengths being differences each between amplitudes associated with two selected types of the selected heart sounds;
durations each associated with a selected type of the selected heart sounds;
electromechanical time intervals each between a selected type of the selected heart sounds and a selected type of the selected cardiac electrical events;
mechanical time intervals each between two selected types of the selected type heart sounds; and
fundamental frequencies each associated with a selected type of the selected heart sounds.

23. The method of claim 22, wherein generating values of at least one predetermined parameter comprises generating values of at least one of:
strength of S3 relative to S4;
time interval between S3 and an adjacently subsequent atrial contraction;
time interval between S4 and an adjacently preceding atrial contraction;
time interval between onsets of S3 and second heart sound (S2);
fundamental frequency of S3; and
fundamental frequency of S4.

24. The method of claim 18, wherein generating the values of at least one predetermined parameter comprises generating the values of the at least one predetermined parameter for a predetermined data acquisition duration on a predetermined periodic basis.

25. The method of claim 18, further comprising generating an alert signal indicative of a predetermined cardiac condition based on the at least one trend.

26. The method of claim 25, wherein producing the at least one trend comprises producing at least one trend related to at least one of third heart sound (S3) and fourth heart sound (S4).

27. The method of claim 25, wherein generating the alert signal comprises comparing a quantity associated with the at least one trend to a predetermined threshold level.

28. The method of claim 27, wherein generating the alert signal comprises generating the threshold based on values of the at least one predetermined parameter measured during a second predetermined period of time.

29. The method of claim 27, wherein generating the alert signal comprises generating an alert signal indicative of a change in one of diastolic filling patterns.

30. The system of claim 18, wherein delivering the at least one therapy comprises delivering a drug therapy that relieves an elevated left atrial filling pressure.

31. The method of claim 18, wherein generating values of at least one predetermined parameter comprises generating relative strengths being differences each between amplitudes associated with two selected types of the selected heart sounds.

32. The method of claim 18, wherein generating values of at least one predetermined parameter comprises generating fundamental frequencies each associated with a selected type of the selected heart sounds.

33. A cardiac rhythm management system for treating a patient, comprising:
an implantable device including:
an acoustic sensor including an accelerometer adapted to sense an acoustic energy to produce an acoustic sensor signal indicative heart sounds of the patient and physical activities of the patient;
a signal conditioning circuit coupled to the acoustic sensor, the signal conditioning circuit adapted to filter the acoustic sensor signal to reduce noise in the acoustic sensor signal;
a cardiac sensing circuit to sense at least one cardiac signal indicative of cardiac electrical events;
a gating module coupled to the signal conditioning circuit and the cardiac sensing circuit, the gating module adapted to generate heart sound detection windows each timed for detection of one of selected heart sounds based on a time of occurrence of one of selected cardiac electrical events;
a heart sound detector, coupled to the gating module, to detect the selected heart sounds indicative of ventricular diastolic hemodynamic performance;
a parameter generator coupled to the heart sound detector, the parameter generator adapted to generate values of at least one predetermined parameter related to the selected heart sounds using the acoustic sensor signal and including a noise monitoring module and a screening module, the noise monitoring module adapted to produce a background noise level indicative of the physical activities of the patient using the acoustic sensor signal, the screening module adapted to exclude the values of the at least one predetermined parameter generated using the acoustic sensor signal sensed when the background noise level exceeds a predetermined level; and
a therapy circuit coupled to the measurement module, to deliver a therapy based on the values of the at least one predetermined parameter; and
an external system communicatively coupled to the implantable device via telemetry, the external system including a processor communicatively coupled to the measurement module, the processor adapted to perform a statistical process analyzing the values of the at least one predetermined parameter generated for a predetermined duration and produce at least one trend quantitatively presenting one or more ventricular diastolic filling pattern changes during the predetermined duration using an outcome of the statistical process.

34. The cardiac rhythm management system of claim 33, wherein the implanted device is housed in a hermetically sealed metal can, and the acoustic sensor resides within the metal can.

35. The cardiac rhythm management system of claim 33, further comprising a lead having a proximal end coupled to the implantable device and distal end disposed in or about a heart, wherein the acoustic sensor is connected to the lead at or near the distal end.

36. The cardiac rhythm management system of claim 33, wherein the measurement module comprises at least one of:
 a strength detector adapted to measure amplitudes each associated with a selected type of the selected heart sounds;
 a relative strength detector adapted to determine differences each between amplitudes associated with two selected types of the selected heart sounds;
 a duration timer adapted to measure durations each associated with a selected type of the selected heart sounds;
 an electromechanical interval timer adapted to measure time intervals each between a selected type of the selected heart sounds and a selected type of the selected cardiac electrical events;
 a mechanical interval time adapted to measure time intervals each between two selected types of the selected type heart sounds; and
 a frequency analyzer adapted to compute a fundamental frequency associated with a selected type of the selected heart sounds.

37. The cardiac rhythm management system of claim 33, wherein the implantable device further comprises a processor coupled to the measurement module, the processor including a trending analyzer adapted to produce and analyze at least one trend related to one or more types of the selected heart sounds based on selected values of the at least one predetermined parameter measured during a predetermined period of time.

38. The cardiac rhythm management system of claim 37, wherein the implantable device further comprises an alert signal generator coupled to the trending analyzer, the alert signal generator adapted to generate an alert signal indicative of a predetermined cardiac condition based on an outcome of a trending analysis.

39. The cardiac rhythm management system of claim 38, wherein the therapy circuit includes a therapy controller adapted to execute a predetermined therapy control algorithm to determine therapy parameters based on the values of the at least one predetermined parameter related to the selected heart sounds.

40. The cardiac rhythm management system of claim 33, wherein the external system further comprises an alert signal generator coupled to the trending analyzer, the alert signal generator adapted to generate an alert signal indicative of a cardiac condition based on an outcome of a trending analysis.

41. The cardiac rhythm management system of claim 40, wherein the external system comprises a controller adapted to execute a predetermined therapy control algorithm to determine therapy parameters based on at least one of:
 one or more of the values of the at least one predetermined parameter;
 the at least one trend; and
 the alert signal.

42. The system of claim 33, wherein the at least one predetermined parameter comprises differences each between amplitudes associated with two selected types of the selected heart sounds, and the parameter generator comprises a relative strength detector adapted to determine the differences each between the amplitudes associated with the two selected types of the selected heart sounds.

43. The system of claim 33, wherein the at least one predetermined parameter comprises a fundamental frequency associated with a selected type of the selected heart sounds, and the parameter generator comprises a frequency analyzer adapted to compute the fundamental frequency associated with the selected type of the selected heart sounds.

* * * * *

UNITED STATES PATENT AND TRADEMARK OFFICE
CERTIFICATE OF CORRECTION

| | |
|---|---|
| PATENT NO. | : 7,972,275 B2 |
| APPLICATION NO. | : 10/334694 |
| DATED | : July 5, 2011 |
| INVENTOR(S) | : Krzysztof Z. Siejko et al. |

It is certified that error appears in the above-identified patent and that said Letters Patent is hereby corrected as shown below:

In column 12, line 17, delete "10/323.604," and insert -- 10/323,604, --, therefor.

In column 15, line 61, in Claim 9, delete "based" and insert -- based on --, therefor.

In column 18, line 14, in Claim 30, delete "system" and insert -- method --, therefor.

Signed and Sealed this
Twenty-second Day of November, 2011

David J. Kappos
*Director of the United States Patent and Trademark Office*